US005707801A

United States Patent [19]
Bresser et al.

[11] Patent Number: 5,707,801
[45] Date of Patent: Jan. 13, 1998

[54] MANUAL IN SITU HYBRIDIZATION ASSAY

[75] Inventors: Joel Bresser, Bellaire; Mary Jean Evinger-Hodges, Arlington, both of Tex.

[73] Assignee: Aprogenex, Inc., Houston, Tex.

[21] Appl. No.: 421,705

[22] Filed: Apr. 13, 1995

Related U.S. Application Data

[63] Continuation of Ser. No. 668,751, Mar. 13, 1991, abandoned, which is a continuation of Ser. No. 239,491, Aug. 31, 1988, abandoned.

[51] Int. Cl.$^6$ .................. C12Q 1/68; C12Q 1/70; C12P 19/34; C07H 21/04
[52] U.S. Cl. .................. 435/6; 435/5; 435/91.2; 435/7.1; 435/7.2; 435/7.9; 536/24.3; 536/24.33; 536/23.1; 530/388.1

[58] Field of Search .................. 435/6, 5, 91.2, 435/7.1–7.9; 536/24.3–24.33; 530/388.1

[56] References Cited

U.S. PATENT DOCUMENTS

| | | | |
|---|---|---|---|
| 4,886,741 | 12/1989 | Schwartz et al. | 435/5 |
| 4,888,278 | 12/1989 | Singer et al. | 435/6 |
| 5,047,523 | 9/1991 | Woods et al. | 536/27 |

*Primary Examiner*—W. Gary Jones
*Assistant Examiner*—Dianne Rees
*Attorney, Agent, or Firm*—Elman & Associates

[57] ABSTRACT

A rapid, sensitive in situ hybridization assay is provided which will detect as few as 1–5 copies of target biopolymer per cell and may be accomplished in 2–4 hours. There is provided a quantitative assay which may be used to diagnose and monitor treatment of diseases.

57 Claims, 14 Drawing Sheets

SECONDARY STRUCTURE OF CELLULAR RNA

Temperature Effect on In Situ Hybridizations

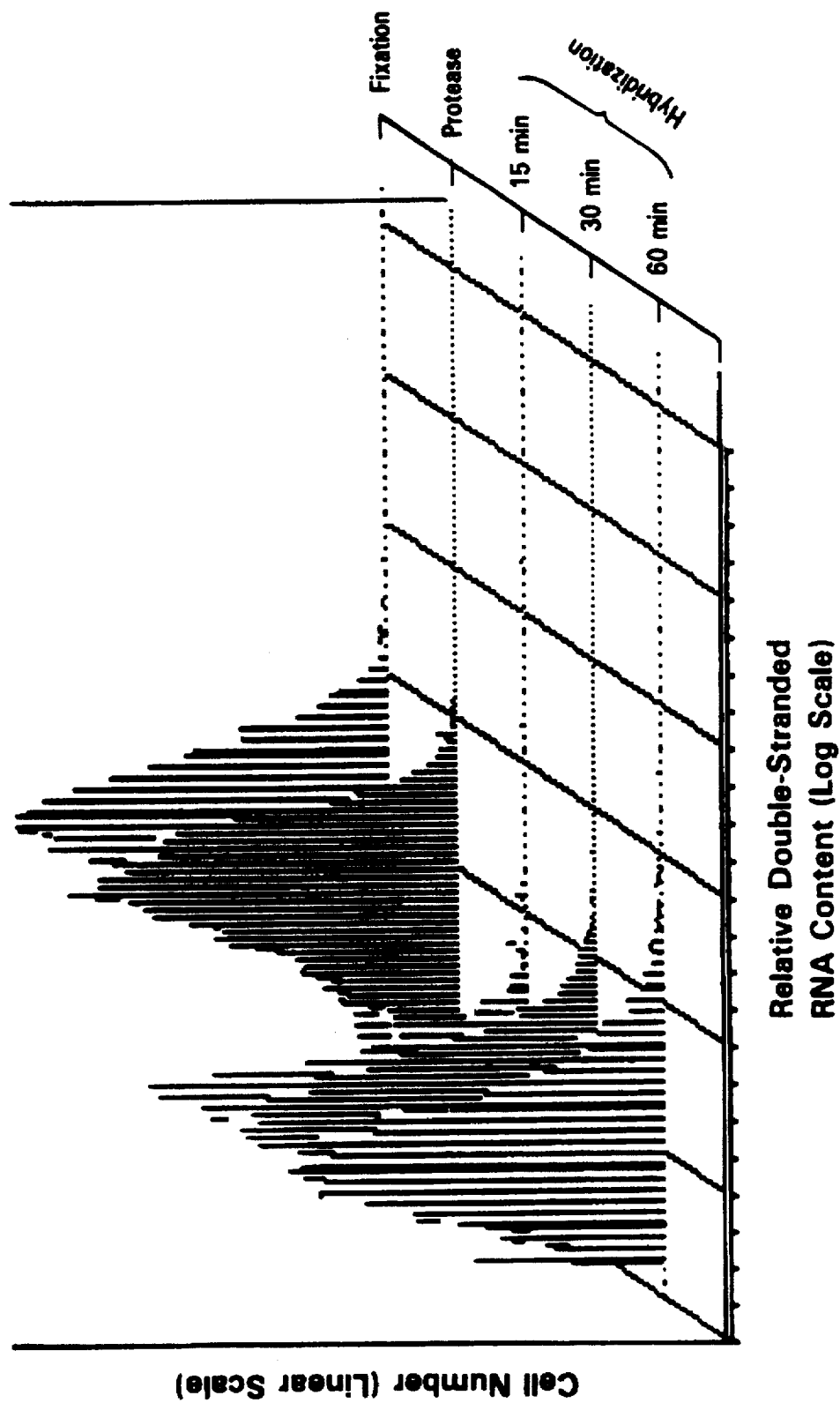

FIG. 7
FIG. 8
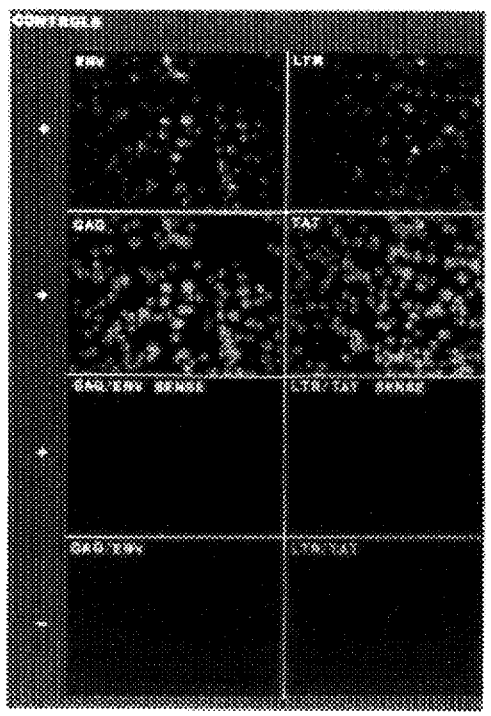
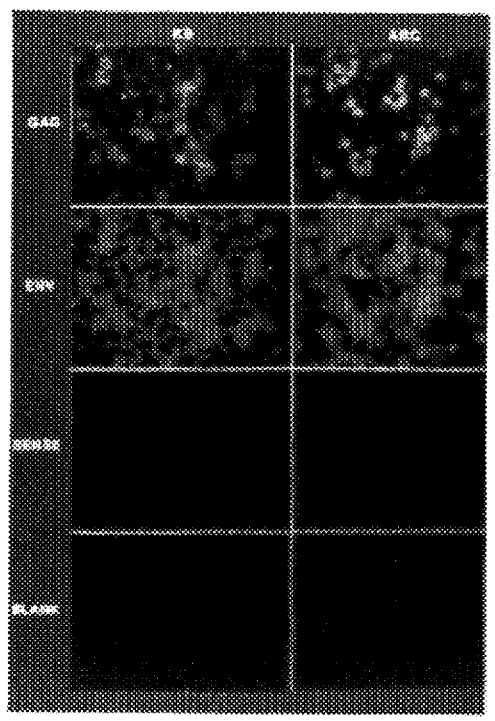

MANUAL IN SITU HYBRIDIZATION ASSAY

CROSS REFERENCE TO RELATED APPLICATIONS

This is a continuation of parent U.S. patent application Ser. No. 07/668,751, filed Mar. 13, 1991, now abandoned, which is a continuation of U.S. patent application Ser. No. 07/239,491, filed Aug. 31, 1988, abandoned.

BACKGROUND OF THE INVENTION

1. Field of the Invention

The present invention relates to the field of in situ hybridization assays useful for detecting as few as 1–5 copies of target nucleic acid per cell. This assay method significantly increases the sensitivity of detection of nucleic acids over other known methods. In addition, this hybridization method is accomplished with far greater speed than has been reported for other in situ assays. This present invention also provides a method for the rapid and sensitive detection of nucleic acids and proteins in the same cell.

2. Description of the Prior Art

In situ hybridization provides a technique for the determination and quantitation of biopolymers such as nucleic acids (DNA and RNA) and proteins in tissues at the single cell level. Such hybridization techniques can detect the presence or absence of specific genes in tissues at the single cell level. In situ hybridization procedures may also be utilized to detect the expression of gene products at the single cell level.

By the use of specific nucleic acid (RNA or DNA) probes, genetic markers for infection and other disease states may be detected. Certain genetic diseases are characterized by the presence of genes which are not present in normal tissue. Other diseased conditions are characterized by the expression of RNAs or RNA translation products (i.e. peptides or proteins) which are not expressed in normal cells. Some disease states are characterized by the absence of certain genes or gene portions, or the absence or alteration of expression of gene products or proteins.

Current methods allow the detection of these markers but are relatively time consuming and of limited sensitivity. Hybridization techniques are based on the ability of single stranded DNA or RNA to pair (or hybridize) with a complementary nucleic acid strand. This hybridization reaction allows the development of specific probes that can identify the presence of specific genes (DNA), or polynucleotide sequences or the transcription and expression of those genes (mRNA).

Solution hybridization methods which require the destruction of the cell and the isolation of the nucleic acids from the cell prior to carrying out the hybridization reaction sacrifice the cellular integrity, spatial resolution and sensitivity of detection. In situ hybridization allows the detection of RNA or DNA sequences within individual cells. In situ hybridization yields greater sensitivity than solution hybridization by means of eliminating the dilution of a particular target gene, nucleic acid, or protein by the surrounding and extraneous RNA and DNA of other cells. In situ hybridization also allows for the simultaneous detection of multiple substances, i.e. genes, nucleic acids or proteins within individual cells, permitting the identification of a particular cell expressing a cellular gene or viral sequence. In addition, since in situ hybridization analysis is performed and quantitated for single cells, minimnal sample and reagents are required.

Prior to the present invention, in situ hybridization procedures were only capable of detecting nucleic acids present at greater than ten copies per cell. Such procedures required at least 8 hours to over 14 days to perform. Prior in situ procedures were neither quantitative nor capable of performing multiple simultaneous detections.

SUMMARY OF THE INVENTION

It is an object of the present invention to provide an in situ hybridization procedure capable of detecting polynucleotides when present at a concentration as low as 1–5 copies per cell.

It is a further object of the present invention to provide an in situ hybridization procedure capable of detecting more than one target molecule in an individual cell.

It is a further object of the present invention to provide an in situ hybridization procedure that could be carried out within about two to four hours.

It is a further object of the present invention to provide an in situ hybridization procedure that could be quantitative for as few as 1–5 molecules of target nucleic acid per cell.

It is a further object of the present invention to provide an in situ hybridization procedure that could simultaneously detect multiple biopolymers.

The present invention provides a method for the detection of biopolymers within individual cells or tissue sections deposited on a solid support. Optimization of each step of the procedure as provided by the present invention allows a rapid, sensitive hybridization assay. Target biopolymer molecules may be quantitated at a level of as few as 1–5 molecules per cell. This hybridization assay may be used to detect levels of polynucleotides in cells such as bone marrow and peripheral blood, in tissue sections or in tissue cultured cells. The hybridization procedure of the present invention can detect polynucleotides in single cells with the sensitivity of as few as 1–5 molecules per cell in as little as 2–4 hours. This procedure also allows for the simultaneous detection of more than one different polynucleotide sequence in an individual cell. The present invention also allows detection of proteins and polynucleotides in the same cell.

Briefly, cells, either as single cell suspensions or as tissue slices were deposited on solid supports such as glass slides. The cells are fixed by choosing a fixative which provides the best spatial resolution of the cells and the optimal hybridization efficiency. After fixation, the support bound cells may be dehydrated and stored at room temperature or the hybridization procedure may be carried out immediately.

The hybridization step is then carried out in a solution containing a chaotropic agent such as 50% formamide, a hybrid stabilizing agent such as five times (5×) concentrated SSC solution (1×=0.15M sodium chloride and 0.015M sodium citrate), a buffer such as 0.1M sodium phosphate (pH 7.4), about 100 micrograms (pg)/milliliter (ml) low molecular weight DNA to diminish non-specific binding, 0.1% Octyl-phenoxy-polyethoxy-ethanol, to facilitate probe entry into the cells and about 10–20 mM vanadyl ribonucleoside complexes.

To the hybridization solution is added a probe, to hybridize with a target polynucleotide. The most preferable probe is a single-stranded RNA probe, approximately 75 to 150 bases in length. An antibody probe may be utilized to bind to a target protein or antigen. The hybridization solution containing the probe is added in an amount sufficient to cover the cells. The cells are then incubated at 55° C. for at least 30 minutes. The probe is added at a high concentration of at least about 1 µg/ml of hybridization solution in order to give optimal results in this time frame.

The probes may be detectably labeled prior to addition to the hybridization solution. Alternatively, a detectable label may be selected which binds to the hybridization product. Probes may be labeled with any detectable group for use in practicing the invention. Such detectable group can be any material having a detectable physical or chemical property. Such detectable labels have been well-developed in the field of immunoassays and in general most any label useful in such methods can be applied to the present invention. Particularly useful are enzymatically active groups, such as enzymes (see Clin. Chem., 22:1243 (1976)), enzyme substrates (see British Pat. Spec. 1,548,741), coenzymes (see U.S. Pat. Nos. 4,230,797 and 4,238,565) and enzyme inhibitors (see U.S. Pat. No. 4,134,792); fluorescers (see Clin. Chem., 25:353 (1979); chromophores; ltmainescers such as chemiluminescers and biolaminescers (see Clin. Chem., 25:512 (1979)); specifically bindable ligands; proximal interacting pairs; and radioisotopes such as $^3H$, $^{35}S$, $^{32}P$, $^{125}I$ and $^{14}C$.

The invention of the present application which provides optimal fixatives allowing probe entry and blocking of non-specific probe binding and formamide hybridization at high temperatures (55° C.) provides a hybridization assay with rapid kinetics of hybrid formation and sensitivity of as few as 1–5 molecules per cell.

The superior results of the invention of the present application is postulated to occur by preventing precipitation of cellular constituents onto mRNA or the covalent modification of mRNA, the destabilization of ribosomal RNA subunit binding, and promotion of accessibility of full length mRNA for hybrid formation by inducing single-strandedness in cellular RNA and/or DNA. The present invention arose out of the applicant's discovery of the strong correlation between cellular RNA single-strandedness and the rapid kinetics of hybridization which yielded a highly sensitive assay procedure.

In one aspect, the present invention provides a simple method to determine the optimal fixation/prehybridization/hybridization/detection conditions for any tissue type so that: (1) single molecules may be detected, (2) cellular morphology will be preserved and (3) the total reaction time will be reduced to 2–4 hours.

Briefly, in order to predict the optimal conditions to achieve this rapid and sensitive hybridization, a cellular specimens in multiple samples, either in suspension or deposited on glass slides, are exposed first to a fixative and subsequently to a hybridization solution.

The fixative is selected from the group consisting of 95% ethanol/5% acetic acid, 75% ethanol/20% acetic acid, 50% methanol/50% acetone and 10% formaldehyde/90% methanol (all v/v). Other useful fixatives will be obvious to one skilled in the art as long as the fixative selected allows at least a 70% shift of double stranded to single stranded cellular polynucleotides while maintaining cellular spatial relationships. The duration of exposure to the fixative is from 1 to 180 min. Preferably, 1 to 30 min., and most preferably 20 min. The temperature of the fixation procedure is preferably −20° to 50° C. and most preferably 20° C. A subsequent exposure to 70% ethanol/30% water for 0.5 min., to 20 min., at −20° to 30° C. may be utilized if samples are to be stored prior to hybridization.

The hybridization solution consists of a chaotropic denaturing agent, a buffer, a pore forming agent, a hybrid stabilizing agent, non-specific nucleotides, and a target specific probe.

The chaotropic denaturing agent (Robinson, D. W. and Grant, M. E. (1966) J. Biol. Chem. 241:4030; Hamaguchi, K. and Geiduscheck, E. P. (1962) J. Am. Chem. Soc. 84:1329) is selected from the group consisting of formamide, urea, thiocyanate, guarddine, trichloroacetate, tetramethylamine, perchlorate, and sodium iodide. Any buffer which maintains pH at least between 7.0 and 8.0 may be utilized. The pore forming agent is for instance, a detergent such as 23-Lauryl-ether, 20-Cetyl-ether, sodium dodecyl sulfate, (3-[(3-Cholamidopropyl)-dimethylammonio]-1-propane-sulphonate, Octyl-phenoxy-polyethoxy-ethanol. Depending on the location of the target biopolymer, the pore-forming agent is chosen to facilitate probe entry through plasma, or nuclear membranes or cellular compartmental structures. For instance, 0.05% 23-Lauryl-ether or 0.1% Octyl-phenoxy-polyethoxy-ethanol will permit probe entry through the plasma membrane but not the nuclear membrane. Alternatively, sodium deoxycholate will allow probes to traverse the nuclear membrane. Thus, in order to restrict hybridization to the cytoplasmic biopolymer targets, nuclear membrane pore-forming agents are avoided. Such selective subcellular localization contributes to the specificity and sensitivity of the assay by eliminating probe hybridization to complementary nuclear sequences when the target biopolymer is located in the cytoplasm. Agents other than detergents such as fixatives may serve this function. Furthermore, a biopolymer probe may also be selected such that its size is sufficiently small to traverse the plasma membrane of a cell but is too large to pass through the nuclear membrane.

Hybrid stabilizing agents such as salts of mono and divalent cations are included in the hybridization solution to promote formation of hydrogen bonds between complementary sequences of the probe and its target biopolymer. Preferably sodium chloride at a concentration from 0.15M to 1M is used; most preferably, the concentration of sodium chloride is 0.6M.

In order to prevent non-specific binding of nucleic acid probes, nucleic acids unrelated to the target biopolymers are added to the hybridization solution at a concentration of 100 fold the concentration of the probe.

Specimens are removed after each of the above steps and analyzed by observation of cellular morphology as compared to fresh, untreated cells using a phase contrast microscope. The condition determined to maintain the cellular morphology and the spatial resolution of the various subcellular structures as close as possible to the fresh untreated cells is chosen as optimal for each step.

In addition, cellular nucleic acids were stained with about 50 µg/ml propidium iodide dye. This dye has a specific characteristic fluorescent emission (about 480 nm, green) when the nucleic acid is single-stranded and emits at a different wave length (about 615 nm, red) when the nucleic acid is double-stranded. The dye utilized may be dependent upon whether the target sequence for the particular assay is RNA or DNA. If the assay is to detect low copy numbers of DNA, then a DNA detecting dye such as acridine orange, tetrahydrofuran, methyl green, pyroDin Y and azure B are used, and the nuclear DNA is analyzed for the amount of single or double-strandedness. If instead, the assay is to be used to detect low copy numbers of RNA, then RNA dye such as Acridines, Azines, Xanthenes, Oxazines, and Thiazines are used and the cytoplasmic RNA is analyzed for the amount of single or double-strandedness. Regardless of whether the assay is used to analyze RNA or DNA, the optimal conditions are reached when the nucleic acid to be detected has undergone a 70% shift from double-strandedness to single-strandedness. When the shift of the secondary structure of the nucleic acid from double-strandedness to single-strandedness has reached at least 70%, and there is no decrease in the total amount of fluorescence, then the conditions have been adjusted according to the present invention and will permit optimal hybridization and detection of as few as 1-5 molecules of target nucleic acid within a single cell. Furthermore, the time required for optimal hybridization can be determined from the omount of time necessary for at least 70% of the cellular nucleic acid to become single-stranded.

In the most preferred embodiment, the hybridization assay of the present invention provides a method for assaying biopolymers in a cell sample having substantially intact membranes comprising the steps of 1) depositing the target cells onto a solid support, 2) fixing the cells, 3) incubating the cells with a hybridization solution containing a single-stranded RNA probe, 4) detecting the amount of probe hybridized to the target nucleic acid. The samples are then washed and the amount of target nucleic acids axe determined by quantitation either photographically through a microscope with fluorescent capabilities or by direct reading of the fluorescence with a Meridian ACAS 470 work station (Meridian Instruments, Okemos, Mich.).

BRIEF DESCRIPTION OF THE DRAWINGS

FIG. 3 demonstrates the changes in secondary structure of cellular RNA as a function of efficiency of the In Situ Hybridization reaction.

FIG. 7 demonstrates the specificity of detection of Human Immunodeficiency Virus (HIV) in positive and negative controls by In Situ Hybridization.

FIG. 8 demonstrates the detection of HIV in patients with Kaposi's Sarcoma (KS) or AIDS Related Complex (ARC) by In Situ Hybridization.

DETAILED DESCRIPTION OF THE INVENTION

Mounting Cells/Tissues

Figure 1:
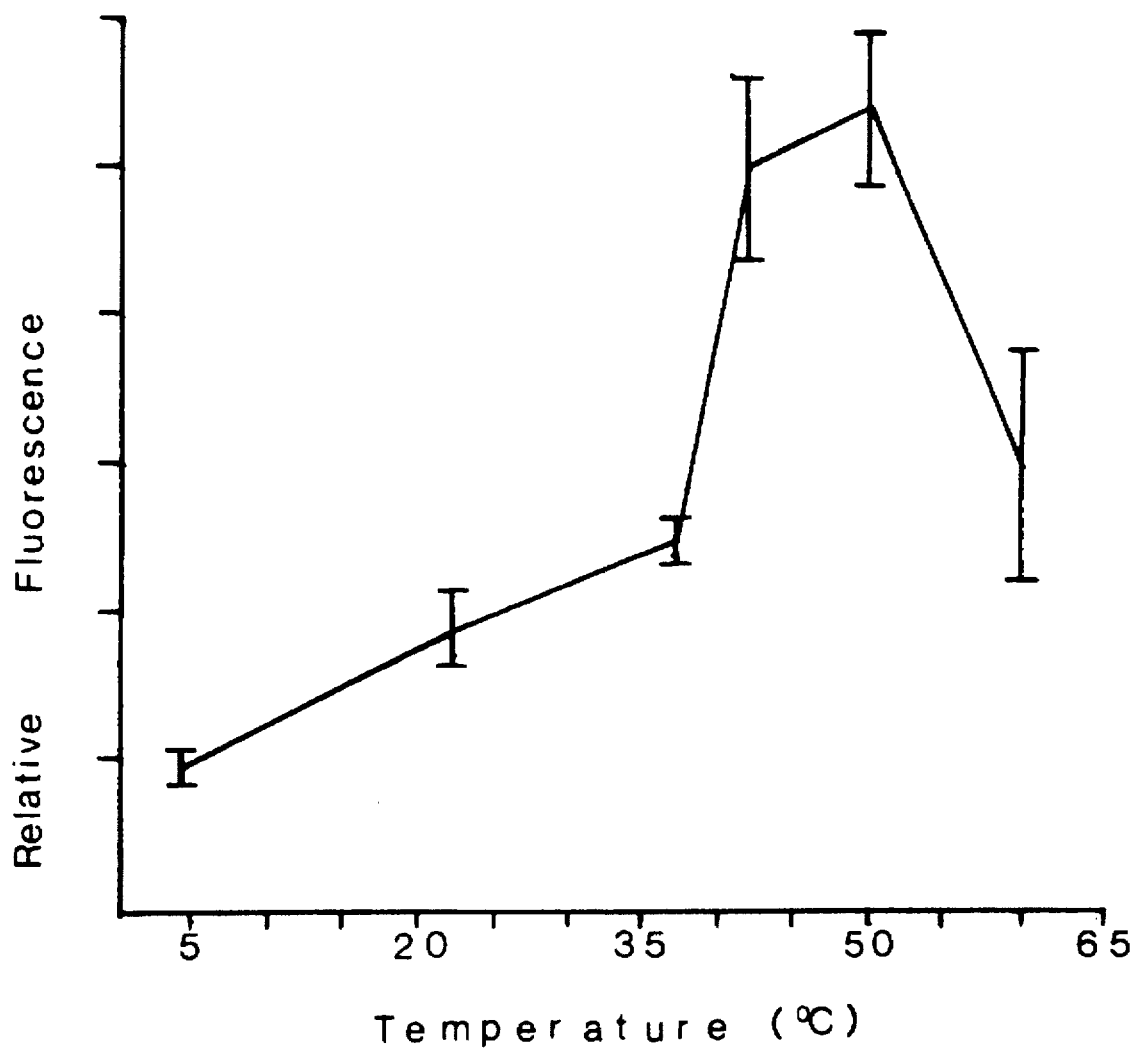
FIG. 1 demonstrates the optimal temperature of the In Situ Hybridization.

The first step in the in situ hybridization procedure is the deposition of specimens onto a solid support. Specimens constitute any material which is composed of or contains cells or portions of cells. The cells may be living or dead, so long as the target biopolymer (DNA, RNA or protein) is unaltered and und3maged and capable of detection. The specimen should contain cells with substantially intact membranes. Although it is not necessary that all membranes of the cellular structure be intact, the membranes must be sufficiently preserved to allow: retention of the target biopolymer, introduction of the detecting probe to the site of the target biopolymer and preservation of antigenicity of any target membrane components.

Techniques for depositing the specimens on the solid support will depend upon the cell or tissue type and may include, for example, standard sectioning of tissue or smearing or cytocentrifugation of single cell suspensions.

Many types of solid supports may be utilized to practice the invention. Supports which may be utilized include, but are not limited to, glass, Scotch tape (3M), nylon, Gene Screen Plus (New England Nuclear) and vitrocellulose. Most preferably glass microscope slides are used. The use of these supports and the procedures for depositing specimens thereon will be obvious to those of skill in the art. The choice of support material will depend upon the procedure for visualization of cells and the quantitation procedure used. Some filter materials are not uniformly thick and, thus, shrinking and swelling during in situ hybridization procedures is not uniform. In addition, some supports which autofluoresce will interfere with the determination of low level fluorescence. Glass microscope slides are most preferable as a solid support since they have high signal-to-noise ratios and can be treated to better retain tissue.

Fixation of Cells/Tissues

After depositing cells or sections on solid supports, the samples are fixed. A fixative may be selected from the group consisting of any precipitating agent or cross-linking agent used alone or in combination, and may be aqueous or non-aqueous. The fixative may be selected from the group consisting of formaldehyde solutions, alcohols, salt solutions, mercuric chloride sodium chloride, sodium sulfate, potassium dichromate, potassium phosphate, ammonium bromide, calcium chloride, sodium acetate, lithium chloride, cesium acetate, calcium or magnesium acetate, potassium nitrate, potassium dichromate, sodium chromate, potassium iodide, sodium iodate, sodium thiosulfate, picric acid, acetic acid, paraformaldehyde, sodium hydroxide, acetones, chloroform, glycerin, thymol, etc. Preferably, the fixative will comprise an agent which fixes the cellular constituents through a precipitating action and has the following characteristics: the effect is reversible, the cellular morphology is maintained, the antigenicity of desired cellular constituents is maintained, the nucleic acids are retained in the appropriate location in the cell, the nucleic acids are not modified in such a way that they become unable to form double or triple stranded hybrids, and cellular constituents are not affected in such a way so as to inhibit the process of nucleic acid hybridization to all resident target sequences. Choice of fixatives and fixation procedures can affect cellular constituents and cellular morphology; such effects can be tissue specific. Preferably, fixatives for use in the invention are selected from the group consisting of ethanol, ethanol-acetic acid, methanol, and methanol-acetone which fixatives afford the highest hybridization efficiency with good preservation of cellular morphology.

Fixatives most preferable for practicing the present invention include 95% ethanol/5% acetic acid for HL-60 and normal bone marrow cells, 75% ethanol/20% acetic acid for K562 and normal peripheral blood cells, 50% methanol/50% acetone for fibroblast cells and normal bone marrow cells, and 10% formaldehyde/90% methanol for cardiac muscle tissue. These fixatives provide good preservation of cellular morphology and preservation and accessibility of antigens, and high hybridization efficiency. According to the present invention, one or two fixatives for each tissue type are provided which ensure both the best spatial resolution of cells and the optimal hybridization efficiency.

Simultaneously, the fixative may contain a compound which fixes the cellular components by cross-linking these materials together, for example, glutaraldehyde or formaldehyde. While this cross-linking agent must meet all of the requirements above for the precipitating agent, it is generally more "sticky" and causes the cells and membrane components to be secured or sealed, thus, maintaining the characteristics described above. The cross linking agents when used are preferably less than 10% (v/v).

Cross-linking agents, while preserving ultrastructure, often reduce hybridization efficiency; they form networks trapping nucleic acids and antigens and rendering them inaccessible to probes and antibodies. Some also covalently modify nucleic acids preventing later hybrid formation.

Storage of Cells/Tissues

After fixation, microscope slides containing cells may be stored air dried at room temperature for up to three weeks, in cold (4° C.) 70% ethanol in water for six to twelve months, or in paraplast for up to two years. If specimens are handled under RNase free conditions, they can be dehydrated in graded alcohols and stored for at least five months at room temperature.

Prehybridization Treatments

According to the present invention no formal prehybridization step is necessary. Blocking nonspecific binding of probe and facilitating probe entry can be accomplished in the hybridization solution. If short hybridizations are to be done (>30 min.), slides may be preheated to hybridization temperature before addition of the hybridization solution.

Hybridizations

Nucleic acid hybridization is a process where two or more complementary strands of DNA, RNA, oligonucleotides, polynucleotides, or any combination thereof that recognize one another and bind together through the formation of some form of either spontaneous or induced chemical bond, usually a hydrogen bond. The degree of binding can be controlled based on the types of nucleic acids coming together, and the extent of "correct" binding as defined by normal nucleic acids coming together, and the extent of "correct" binding as defined by normal chemical rules of bonding and pairing. For example, if the binding of two strands forms 9 out of 10 correct matches along a chain of length 10, the binding is said to be 90% homologous.

Cellular nucleic acid sequences are detected by the process of molecular hybridization. The probe must be "labeled" in some way so to allow "detection" of any complementary cellular nucleic acid sequences present within the individual cells.

In the present invention, the term "hybridization" also means the binding of an antibody to a target antigen.

Types of Probes

A probe is defined as genetic material DNA, RNA, or oligonucleotides or polynucleotides comprised of DNA or RNA and antibodies. The DNA or RNA may be composed of the bases adenosine, uridine, thymidine, guanine, cytosine, or any natural or artificial chemical derivatives thereof. The probe is capable of binding to a complementary target cellular genetic sequence through one or more types of chemical bonds, usually through hydrogen bond formation. The extent of binding is referred to as the amount of mismatch allowed in the binding or hybridization process; the extent of binding of the probe to the target cellular sequences also relates to the degree of complementarity to the target sequences. The size of the probe is adjusted to be of such size that it forms stable hybrids at the desired level of mismatch; typically, to detect a single base mismatch requires a probe of approximately 12–50 bases. Larger probes (from 50 bases up to tens of thousands of bases) are more often used when the level of mismatch is measured in terms of overall percentage of similarity of the probe to the target cellular genetic sequence. The size of the probe may also be varied to allow or prevent the probe from entering or binding to various regions of the genetic material or of the cell. Similarly, the type of probe (for example, using RNA versus DNA) may accomplish these objectives. The size of the probe also affects the rate of probe diffusion, probability of finding a cellular target match, etc. Typically, double-stranded DNA (dsDNA), single-stranded DNA (ssDNA) or RNA probes are used in a hybridization reaction when nucleotide sequences are the target.

Nucleic acid probes can be prepared by a variety of methods known to those of skill in the art. Purified double-stranded sequences of DNA (dsDNA) can be labeled intact by the process of nick translation or random primer extension. The ability of double-stranded probes to hybridize to nucleic acids immobilized within cells is compromised by the ability of the complementary strands to hybridize to each other in solution prior to hybridization with the cellular nucleic acids. Single-stranded DNA (ssDNA) probes do not suffer this limitation and may be produced by the synthesis of oligonucleotides, by the use of the single-stranded phage M13 or plasmid derivatives of this phage, or by reverse transcription of a purified RNA template. The use of single-stranded RNA (ssRNA) probes in hybridization reactions potentially provides greater signal-to-noise ratios than the use of either double or single-stranded DNA probes. Regardless of whether a dsDNA, a ssDNA, or a ssRNA probe is used in the hybridization reaction, there must be some means of detecting hybrid formation. The means of detecting hybrid formation utilizes a probe "labeled" with some type of detectable label.

Antibody probes are known to those skilled in the art. The term "antibody probe" means an antibody that is specific for and binds to any target antigen. Such a target antigen may be a peptide, protein, carbohydrate or any other biopolymer to which an antibody will bind with specificity.

Detection Systems

Detectable labels may be any molecule which may be detected. Commonly used detectable labels are radioactive labels including, but not limited to, $^{32}P$, $^{14}C$, $^{125}I$, $^{3}H$ and $^{35}S$. Biotin labeled nucleotides can be incorporated into DNA or RNA by nick translation, enzymatic, or chemical means. The biotinylated probes are detected after hybridization using avidin/streptavidin, fluorescent, enzymatic or collodial gold conjugates. Nucleic acids may also be labeled with other fluorescent compounds, with immunodetectable fluorescent derivatives or with biotin analogues. Nucleic acids may also be labeled by means of attaching a protein. Nucleic acids cross-linked to radioactive or fluorescent histone HI, enzymes (alkaline phosphatase and peroxidases), or single-stranded binding (ssB) protein may also be used. To increase the sensitivity of detecting the collodial gold or peroxidase products, a number of enhancement or amplification procedures using silver solutions may be used.

An indirect fluorescent immunocytochemical procedure may also be utilized (Rudkin and Stollar (1977) *Nature* 265:472; Van Prooijen, et al (1982) *Exp. Cell. Res.* 141:397). Polyclonal antibodies are raised against RNA-DNA hybrids by injecting animals with poly(rA)-poly(dT). DNA probes were hybridized to cells in situ and hybrids were detected by incubation with the antibody to RNA-DNA hybrids.

According to the present invention RNA probes are preferable to DNA probes (5–8 fold more efficient). Labeling probes with Photobiotin instead of biotin increased the sensitivity of the assay another 2–3 fold.

Probe Size and Concentration

The length of a probe affects its diffusion rate, the rate of hybrid formation, and the stability of hybrids. According to the present invention, small probes (50–150 bases) yield the most sensitive, rapid and stable system. A mixture of short probes (50–150 bases) are prepared length of the target bilength of the target biopolymer to be detected. For ex biopolymer were 1000 bases long, about 10–20 "different" probes of 50–100 bases would be used in the hybrid solution to completely cover all regions of the target biopolymer.

The concentration of the probe affects several parameters of the in situ hybridization reaction. High concentrations are used to increase diffusion, to reduce the time of the hybridization reaction, and to saturate the available cellular sequences. According to the present invention, the reaction is complete after 30 minutes (see FIG. 2). To achieve rapid reaction rates while maintaining high signal-to-noise ratios, probe concentrations of 2.5–5.0 µg/ml are preferable. Most preferable is use of probes at a concentration of 2.5 µg/ml.

Hybridization Solution and Temperature

In a preferred embodiment, the hybridization solution of the present invention consists of 50% formamide, 4× SSC (1× SSC=0.15M sodium chloride and 0.015M sodium citrate), about 0.1M sodium phosphate (pH 7.4), about 100 µg/ml low molecular weight DNA, 0.1% Octyl-phenoxy-polyethoxy-ethanol and about 10–20 mM vanadyl ribonucleoside complexes. Single-stranded RNA probe is added to this solution. The probe may be at least 15–20 bases, preferably, 75–150 bases, and labeled with Photobiotin. As shown in FIG. 1 the most preferable optimal temperature of hybridization is 50°–55° C. However, temperatures ranging from 15° C. to 80° C. may be used.

Post-Hybridization Treatments and Detections

The present invention does not require wash steps prior to hybrid detections. Instead, avidin or streptavidin fluorescent, enzymatic or collodial gold complexes may be added directly to the slides containing hybridization cocktail and incubated for twenty minutes at room temperature, or ten minutes at 37° C. This step constitutes a significant advantage over prior hybridization techniques due to the time saved by eliminating several post-hybridization washing steps and the necessary re-blocking of non-specific avidin/streptavidin binding sites; it results in no decrease in signal or increase in noise.

The streptavidin/avidin detection step is followed by washes in large volumes of 2× SSC/0.1% Octyl-phenoxy-polyethoxy-ethanol. The solution may contain RNase A and T1 at room temperature. This wash can be very short (less than 5 minutes) as long as a continuous gentle circulation or stream of sufficient volume (about 1–200 ml per cm² area of cells) of solution passes over the cells. This may be followed by washes at higher stringency (lower salt concentrations such as at least 0.1× SSC and/or higher temperatures up to 65° C.). Leaving the cell area moist, supports are then dried and coverslipped by any conventional method.

Analysis of the Results of In Situ Hybridizations

Speed, Sensitivity and Quantitation of In Situ Hybridizations

The method of the present invention requires two to four hours to complete with a sensitivity of as few as 1–5 molecules of target biopolymers per cell. This results from the combination of at least three factors: 1) cellular constituents are not irreversibly precipitated onto the nucleic acids; 2) the fixation was optimized for the particular tissue used; and, 3) the kinetics of the reaction proceed more rapidly at high probe concentrations and at elevated temperatures.

The number of copies of mRNA per cell can be estimated from the number of grains over cells when radioactive probes are used. With fluorescent or enzymatic detections a relative estimate of fluorescence or precipitated colored products allows estimation of mRNA copy number. Usually, the approximation of copy number is easier after manual photography, film processing and comparisons of photographic prints.

The quantitation of radioactive or fluorescent signals obtained after in situ hybridizations may be automated by use of an image analysis system, such as the Meridian ACAS 470 workstation as is demonstrated in Example 11.

Simultaneous Detection of Three mRNAs

The present invention allows simultaneous detection of different substances (mRNAs and proteins) within the same cells. This may be accomplished in one of two ways. First, multiple probes each containing a unique label (for example, fluorescent tags "A", "B" and "C" which each emit light at a different detectable wave length) are all added together in the hybridization solutions. Alternatively, a hybridization and detection reaction may be carried out with one probe and label, residual unreacted probe and label washed away under nuclease-free conditions, and another hybridization reaction is carried out. This process is repeated as many times as desired. Example 9 demonstrates one embodiment of the detection of multiple target biopolymers in the same cell.

The following examples are offered by way of illustration and are not intended to limit the invention in any manner. In all examples, all percentages are by weight if for solids and by volume if for liquids, and all temperatures are in degrees Celcius unless otherwise noted.

EXAMPLE 1

Preparation of Probes

A. General

RNA or DNA probes useful in the present invention may be prepared according to methods known to those of skill in the art or may be obtained from any commercial source. RNA probes may be prepared by the methods described by Green et al. (1981) *Cell* 32:681. DNA probes may be prepared by methods known to those of skill in the art such as described by Rigby et al. (1977) *J. Mol. Biol.* 113:237. Synthetic oligonucleotide probes may be prepared as described by Wallace, et al (1979) *Nucleic Acids Research* 6:3543. The probes useful in the present invention must have the following characteristics:

1. Specificity for the target molecule, and
2. At least 15 base pairs in length and preferably 75–150 base pairs.

B. Preparation of RNA probes.

Sub genomic fragments of the c-myc, c-sis, or c-abl genes were obtained from Amersham Inc. (Catalogue nos. RPN.1315X, RPN.1324X, and RPN. 1325X, respectively). In one embodiment of the present invention, sense strand probe of the c-myc, c-abl and c-sis genes were utilized. The c-myc probe used was a 1.3 Kb ClaI/EcoRI genomic clone from the 3' end of the c-myc gene (Dalla-Favera, et al. (1983) *Science* 219:963). The c-abl probe was derived from a subclone of the human c-abl gene, an EcoRI/BamHI fragment corresponding to the 5' c-abl hybridizing region (de Klein et al. (1982) *Nature* 300:765). The c-sis probe was a BamHI fragment of clone L33 corresponding to the 3' end of c-sis (Josephs et al. (1983) *Science* 219:503). The HIV and EBV probes were obtained from and prepared as described in Dewhurst, et al. (1987) *FEBS Lett.* 213:133. The CMV probe was described in Gronczol, et al. (1984) *Science* 224:159. These template plasmid DNAs were transcribed as described by Green et al. (1981) *Cell* 32:681. The size and quantity of the RNA was confirmed by electrophoresis through a denaturing agarose gel as described by Thomas (1980) *Proc. Nat. Acad. Sci. USA* 7–7:5201 and spectrophotometric measurement performed at A260 and A280. A DNA beta-actin probe prepared as described in Cleveland, et. al. (1980) *Cell* 20:95 and the RNA probes were labeled with Photobiotin as described by Bresser and Evinger-Hodges (1987) *Gene Anal. Tech.* 4:89, incorporated herein by reference.

Low-molecular weight DNA was added at a concentration of 100 that of the probe, and all polynucleotides were precipitated by the ⅕ vol. 10M ammonium acetate and 2½ vol. of 95% ethanol. The nucleic acids were recovered by centrifugation and resuspended in water at a concentration of 1 microgram (μg)/microliter (ml) of probe and stored at −70° C. until used.

C. Preparation of Antibody Probes

Antibody probes specific for antigens such as viruses or specific determinants thereof, peptides and proteins derived from a variety of sources, carbohydrate moieties and a wide variety of biopolymers are known to those of skill in the art. The methods for preparation of such antibodies are also known to those of skill in the art.

Briefly, polyclonal antibodies may be prepared by immunization of an animal host with an antigen. Preferably, the antigen is aclministered to the host subcutaneously at weekly intervals followed by a booster dose one month after the final weekly dose. Subsequently, the serum is harvested, antibodies precipitated from the serum and detectably labeled by techniques known to those of skill in the art.

Monoclonal antibodies may be prepared according to any of the methods known to those in the art. Fusion between myeloma cells and spleen cells from immunized donors has been shown to be a successful method of producing continuous cell lines of genetically stable hybridoma cells capable of producing large amounts of monoclonal antibodies against target antigens such as, for instance, tumors and viruses. Monoclonal antibodies may be prepared, for instance, by the method described in U.S. Pat. No. 4,172,124 to Koprowski, et al. or according to U.S. Pat. No. 4,196,265 to Koprowski, et al.

Procedures for labeling antibodies are known to those of skill in the art.

EXAMPLE 2

Temperature Effect on Hybridization

K562 cells (ATCC # CCL 243) were grown in Hank's Balanced Salt Solution supplemented with 10% fetal calf serum. Dividing cells were deposited onto glass slides by cytocentrifugation. Cells were fixed with 75% ethanol, 20% glacial acetic acid, 5% water for 20 minutes at room temperature. No prehybridization step was performed. Twenty microliters of hybridization solution consisting of 50% formanaide, 4× SSC, 0.1M sodium phosphate (pH 7.4), 0.1% Octyl-phenoxy-polyethoxy-ethanol, 100 μg/ml low molecular weight DNA (sheared herring sperm DNA obtained from Sigma Chemical Company) and 2.5 μg/ml of either c-myc, c-abl or c-sis anti-sense RNA probe labeled with Photobiotin was added to each specimen. The anti-sense RNA probes were prepared as described in Example 1. The hybridization reactions were carried out at various temperatures ranging from 4° to 80° C. After incubation at the desired temperatures for two hours, hybrid formation was detected. To detect hybridization, streptavidin fluorescein or rhodamine complexes at 2× the manufacture's recommended concentration was added to this specimen. After incubation at room temperature for 30 min. the specimens were then gently washed with 1 to 200 ml per centimeter square of cell area with each of the following solutions containing 0.1% Octyl-phenoxy-polyethoxy-ethanol in order: 2× SSC, 1× SSC, 0.5× SSC and 0.1× SSC. One drop of a 50/50 (v/v) 100% glycerol/2× PBS solution was added to each specimen. Using a Nikon fluorescent microscope with photomultiplier tube attachments the fluorescence emitted per cell was recorded on each slide hybridized at a different temperature. Approximately 300 to 800 cells were analyzed per slide. Numerical results obtained indicating the amount of fluorescence from each cell were graphically represented as relative fluorescence versus the temperature of hybridization.

The results shown of FIG. 1 demonstrate that hybridization temperatures of 50° C. to 55° C. yields the most relative fluorescence corresponding to the most hybrid formation in the present in situ hybridization invention.

EXAMPLE 3

Kinetics of In Situ Hybridization

Figure 2:
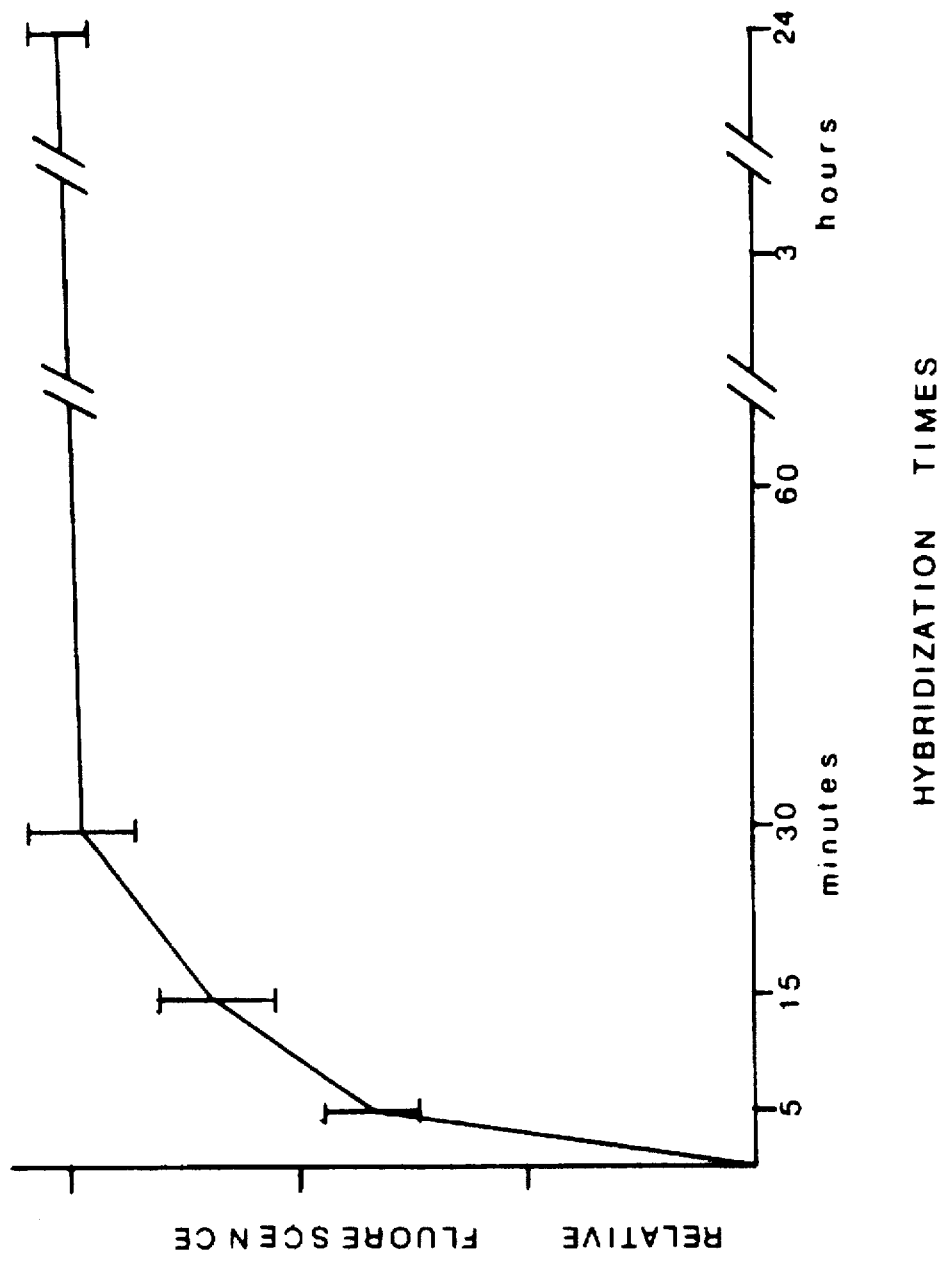
FIG. 2 demonstrates the kinetics of the In Situ Hybridization reaction.

FIG. 2 shows the relationship between the time of hybridization and the amnount of fluorescent signal seen over cells. K562 cells (ATCC #CCL 243) were grown in Hank's Balanced Salt Solution supplemented with 10% fetal calf serum. Dividing cells were deposited onto glass slides by cytocentrifugation. Cells were fixed with 75% ethanol, 20% glacial acetic acid, 5% water for 20 minutes at room temperature. No prehybridization step was performed. Twenty microliters of hybridization solution consisting of 50% formamide, 4× SSC, 0.1M sodium phosphate (pH 7.4), 0.1% Octyl-phenoxy-polyethoxy-ethanol, 100 µg/ml low molecular weight DNA (sheared herring sperm DNA obtained from Sigma Chemical Company) and 2.5 µtg/ml of either c-myc, c-abl or c-sis anti-sense RNA probe labeled with Photobiotin was added to each specimen. The anti-sense RNA probes were prepared as described in Example 1. The hybridization reactions were carried out at various times ranging from 5 minutes to 96 hours. After incubation at 55° C. for the desired time, hybrid formation was detected. To detect hybridization, streptavidin-fluorescein or rhodamine complexes at 2× the manufacturers concentration were added to the specimen. After incubation at room temperature for 30 minutes the specimens were then gently washed with 0.1× SSC/0.1% Octyl-phenoxy-polyethoxy-ethanol at 1–200 ml per cm2 of cell area. One drop of a 50/50 (v/v) 100% glycerol/2× PBS solution was added to each specimen. Using a Nikon fluorescent microscope with photomultiplier tube attachments, the fluorescence emitted per cell was recorded on each slide hybridized at each different time point. Approximately 300 to 800 cells were analyzed per slide. Numerical results obtained indicating the amount of fluorescence from each cell were graphically represented as relative fluorescence versus the time of hybridization. FIG. 2 demonstrates that the hybridization reaction is essentially complete after 30 minutes under the conditions of the present invention.

EXAMPLE 4

Changes in Secondary Structure of Cellular RNA

HL60 cells (ATCC # CCL 240) were grown in Hank's Balanced Salt Solution (BSS) supplemented with 10% fetal calf serum. Cells were harvested and deposited onto glass microscope slides by cytocentrifugation. Cells were air dried on glass slides and stored at room temperature until used. Cells are fixed in one of any number of fixatives for this type of experiment. Typical fixatives would include 70% ethanol, 95% ethanol/5% glacial acetic acid, 75% ethanol, 20% glacial acetic acid, 100% methanol, 100% acetone, 50% acetone, 50% methanol, 4% paraformaldehyde, 2% paraformaldehyde, 10% formaldehyde/90% methanol. After cells were fixed in these fixatives at the appropriate time and temperature, slides were removed from the fixative and stained with Wright Giemsa or hematoxylin and eosin by standard laboratory methods. Cell morphology was assessed by comparing the degree of preservation of morphology after fixation to the morphology prior to fixation.

Fixatives which did not effectively retain visual morphology were arbitrarily rated as +1. Fixatives which effectively retained cellular morphology were arbitrarily rated as between +1 and +4 with the most effective morphologic preservation of cellular morphology rated at +4.

A second evaluation as to the effective preservation of cells by these fixatives was carried out when it was desirable to detect cellular antigens. In this case, cells were removed from the fixatives and incubated with an antibody specific for a particular target cellular antigen. Again, fixatives which effectively maintained antigenicity of cellular components were arbitrarily rated as +4, while fixatives which did not effectively maintain preservation of cellular antigens were rated lower, the worst as +1. Fixatives which scored as +3 or +4 in terms of preservation of cellular morphology and/or preservation of cellular antigenicity were then used in the following steps:

Fresh slides containing untreated cells were fixed in these fixatives and were incubated in hybridization solution containing 50% formamide, 4× SSC, 0.1M sodium phosphate, (pH 7.4), 0.1% Octyl-phenoxy-polyethoxy-ethanol, 100 µg/ml low molecular DNA (sheared herring sperm DNA obtained from Sigma Chemical Company). No biopolymer probe was included in this solution. The cells were incubated in hybridization solution at 50°–55° C. for 5, 10, 15, 20, 30, 45, 60, 90, and 120 minutes. After the completion of this hybridization step, cell samples were washed gently with 1–200 ml per square centimeter of cell area with each of the following solutions containing 0.1% Octyl-phenoxy-polyethoxy-ethanol, 2× SSC, 1× SSC, 0.5× SSC, 0.1× SSC.

The cellular sample was then evaluated as above for preservation of cellular morphology and/or preservation of cellular antigenicity. The cell sample was then further evaluated by staining the cells with 50 µg/ml of propidium iodide. The propidium iodide will stain double stranded and single stranded nucleic acids within the cell. When this dye stains double stranded or single stranded nucleic acids it has a different characteristic emission spectra upon ultraviolet excitation. An untreated cell sample on a slide is also stained.

The total amount of emitted fluorescence is determined on the untreated cell sample using a Nikon fluorescence microscope with a photomultiplier tube attachment. 300–1000 cells are recorded as to the total amount of fluorescence generated from cytoplasmic double stranded RNA content. This measurement then represents a base line level for the total fluorescence in the cytoplasm; that is, the total RNA in the cytoplasm and that RNA being present in a 100% state of double strandedness.

The slides which have been taken through the various fixation and hybridization procedures and times are similarly analyzed. In all cases it is important to chose a fixation and hybridization condition and time which will maintain the same quantity of fluorescence in the cytoplasm of the cell. During hybridization, the fluorescence emitted from the RNA of the cytoplasm of the cell due to the staining of the propidium iodide will change. The emission pattern decreases relative to the double strandedhess of the RNA. Simultaneously, the wave length emission which is reflective of the amount of single stranded RNA in the cytoplasm will begin to increase. When the total fluorescence in the cytoplasm due to RNA has remained the same and the amount of fluorescence due to the amount of double stranded RNA in the cytoplasm has decreased approximately 70% while the amount of fluorescence corresponding to the single stranded RNA within the cytoplasm has increased an equal value, then conditions have been obtained which will allow the detection of 1-5 molecules of RNA within the cytoplasm.

The time of the hybridization reaction which was required to obtain this shift from double stranded to single strandedness of the RNA in the cytoplasm is reflective of the time necessary for an actual hybridization reaction to detect 1-5 molecules per cell of RNA.

Specifically, in FIG. 3, the relative amount of double stranded RNA content is graphically represented on the bottom scale. As the RNA in the cytoplasm becomes more double stranded, the more to the right the curves will fall. The greater the shift in the amount of double strandedness to single strandedness of RNA in the cytoplasm, the greater the shift will be of the curves from the right to the left. The vertical axis represents the cell numbers that were counted. In other words if 300-1000 cells were counted, the vast majority of them fell within a particular area of double strandedness. While some cells had more double strandedness and some had less double strandedness, the analysis can be represented as a bell shaped curve. On the right hand side of the figure is shown the various treatments carried out. The result of staining untreated cells with propidium iodide is not shown. However, after treating HL60 cells with various fixatives the amount of double strandedness of cellular RNA remained essentially the same. Even if a prehybridization treatment is carded out which includes a protease treatment there is essentially no change in the amount of RNA double strandedness.

The curve in FIG. 3 corresponding to the protease treatment is in the same location as the curve for the fixation treatment. It has shifted neither left nor right. However, after fifteen minutes in a hybridization solution, the curve representing the amount of RNA double strandedness has shifted at least 70% to the left. This corresponds to a change in at least 70% of the amount of material in the cytoplasm of the cell becoming single stranded. Comparing this graph to FIG. 2 indicates that after 15 min. in the hybridization cocktail, not only is 70% of the RNA in the cytoplasm of the cell single stranded, but as seen in FIG. 2, 70% of the hybridization reaction is complete.

EXAMPLE 5

Detection of c-myc Oncogene

Balb/c 3T3 cells (ATCC # CCL 163) were grown to density arrest in medium on 8-chamber slides (Tissue-Tek, Miles Laboratories). The medium [Hank's Balanced Salt Solution (BSS) supplemented with 10% fetal calf serum (FCS)] was replaced with serum free medium and the cells serum starved overnight. Multiple specimens were then incubated either in the presence or absence of 15% FCS in Hanks BSS for 45 min. at 37° C.

Cells were fixed with 50% acetone and 50% methanol for 20 minutes at room temperature.

No prehybridization step was performed. 20 µl of hybridization solution consisting of 50% formamide, 4× SSC, 0.1M sodium phosphate (pH 7.4), 0.1% Octyl-phenoxy-polyethoxy-ethanol, 100 µg/ml low molecular weight DNA (sheared herring sperm DNA obtained from Sigma Chemical Co.) and 2.5 µg/ml c-myc anti-sense RNA probe labelled with Photobiotin, was added to each specimen. The c-myc antisense RNA probe was prepared as described in Example 1. After incubation for 2 hrs. at 55° C., hybrid formation was detected.

To detect hybrids, a streptavidin-fluorescein complex (Guesdon, J. L., et al (1979) *J. Histochem. Cytochem.* 27:1131) at 2× the manufacturer's recommended concentration (Bethesda Research Laboratories; Catalog #9538SA; recommended concentration: 7.5 µg/ml) was added to the specimen. After incubation at room temperature for 30 minutes, the specimens were gently washed sequentially (1-200 ml per cm² of cell area) with each of the following solutions containing 0.1% Octyl-phenoxy-polyethoxy-ethanol in order: 2× SSC, 1× SSC, 0.5× SSC, and 0.1× SSC. One drop of a 50/50 (v/v) 100% glycerol/2× PBS solution was added to each specimen. Specimens were photographed with high speed film (Kodak EES135, PS 800/1600) at 1600 ASA for a 20 sec. exposure on a Nikon Photophot microscope at 400× magnification using a standard filter combination for transmission of fluorescent light.

Figure 4A:
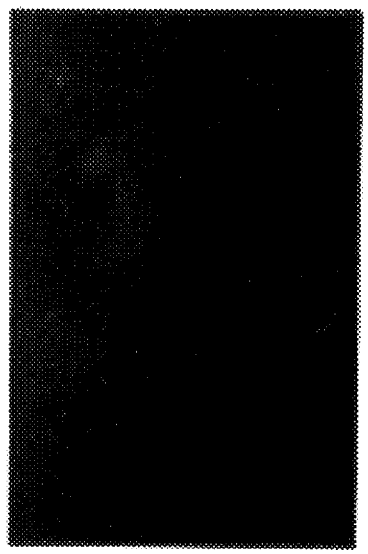
FIG. 4A and B demonstrate the sensitivity of the In Situ Hybridization reaction using a control cell line, Balb/c3T3.
Figure 4B:
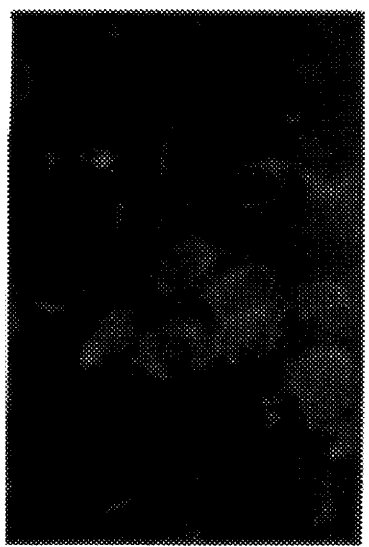

It has been shown by conventional methods (mRNA dot blots, Northern blots, and solution hybridizations) that the c-myc oncogene is not expressed in serum starved cells but 1-10 copies per cell are induced in sexism stimulated cells. (Armelin et al. (1984) *Nature* 310:656). Cells probed for expression of c-myc mRNA by the in situ hybridization procedure of the present invention are shown in FIG. 4A and FIG. 4B. No c-myc mRNA was detected in serum starved Balb/c 3T3 cells (FIG. 4A) while 1 to 10 copies of c-myc mRNA was detected in serum stimulated cells by the method of the present invention (FIG. 4B).

EXAMPLE 6

Detection of Oncogenes in Peripheral Blood Cells and Bone Marrow Cells

Ten ml., of human peripheral blood or 2 ml., of human bone marrow cells were incubated at 37° C. in a 1.2% (215 mOs) ammonium oxalate solution to lyse the red blood cells. The white blood cells were centrifuged at 3,000 rpm for 10 minutes in a clinical centrifuge. The cell pellet was subsequently washed with 10 ml. PBS and the pellet was resuspended in PBS. Cells were deposited by cytocentrifugation onto precleaned glass slides and air dried for 5 min. The cells were then fixed in 75% ethanol/20% acetic acid for 20 min. at room temperature.

No prehybridization step was performed. 20 µl of hybridization solution consisting of 50% formamide, 4× SSC, 0.1M sodium phosphate (pH 7.4), 0.1% Octyl-phenoxy-polyethoxy-ethanol, 100 µg/ml low molecular weight DNA (sheared herring sperm DNA obtained from Sigma Chemical Co.) and 2.5 µg/ml of either c-myc, c-sis, or c-abl anti-sense RNA probe labelled with Photobiotin, was added to each specimen. The anti-sense RNA probes were prepared as described in Example 1. After incubation for 2 hrs. at 55° C., hybrid formation was detected.

To detect hybrids, streptavidin fluorescein complex at 2× the manufacturer's recommended concentration was added to the specimen. After incubation at room temperature for 30 minutes, the specimens were then gently washed (1-200 ml per cm² of cell area) with each of the following solutions containing 0.1% Octyl-phenoxy-polyethoxy-ethanol, in order: 2× SSC, 1× SSC, 0.5× SSC, and 0.1× SSC. One drop of a 50/50 (v/v) 100% glycerol/2× PBS solution was added to each specimen. Specimens were photographed with high speed film (Kodak EES135, PS 800/1600) at 1600 ASA for 20 sec. exposure on a Nikon Photophot microscope at 400× magnification using a standard filter combination for transmission of fluorescent light.

Figure 5:
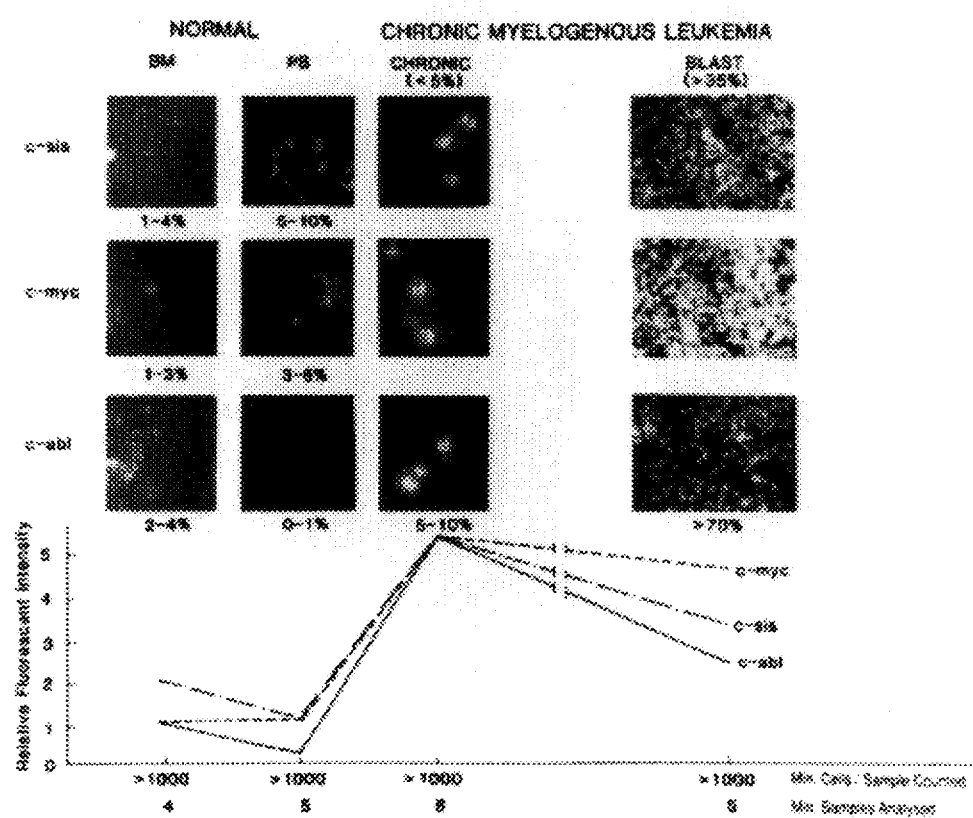
FIG. 5 demonstrates the detection of oncogenes in normal peripheral blood, normal bone marrow and chronic myelogenous leukemia (CML) by In Situ Hybridization.

FIG. 5 depicts the results from in situ hybridization studies on the expression of three different oncogenes in normal bone marrow (BM), normal peripheral blood (PB), or the peripheral blood from patients with chronic myelogenous leukemia (CML). Blood was obtained from these patients when they were either in the chronic stage of the disease or in the blast stage of the disease. In FIG. 5, on the left hand side is shown the three different oncogenes which were analyzed, c-sis, c-myc and c-abl. The numbers below the prints for BM or PB indicate the percent of cells in that sample which are expressing the oncogene indicated on the left. To the bottom of each column of prints (titled BM, PB, chronic or blast) is shown a graphic representation of the relative fluorescent intensity obtained after the hybridizations. The relative fluorescent intensity is indicative of the amount of RNA present within each cell and is scored on a per cell basis. CML in the chronic phase is defined as having less than 5% of the cells in the peripheral blood exist as blasts. In reality, we find that 5–10% of the cells in the peripheral blood are over expressing the three genes which were studied. The expression of these genes is also considerably elevated as compared to either normal BM or PB as seen both in the prints and below the prints on the graph. In the blast phase of the disease which is defined as having greater than 35% of the cells in the peripheral blood exist as blasts, we find that greater than 70% of the cells are typically expressing the three oncogenes c-sis, c-myc, and c-abl. The expression of these genes is elevated when compared to normal bone marrow or normal peripheral blood but is lower than the expression of these genes on a per cell basis in the chronic phase of the disease as seen both in the prints and in the graphic representation.

EXAMPLE 7

Oncogene Detection in Solid Tissue

Four-micron thick frozen sections of human breast tissue obtained from surgically removed biopsy samples were mounted on precleaned glass slides and fixed with 50% methanol/50% acetone for 20 min. at room temperature.

Figure 6:
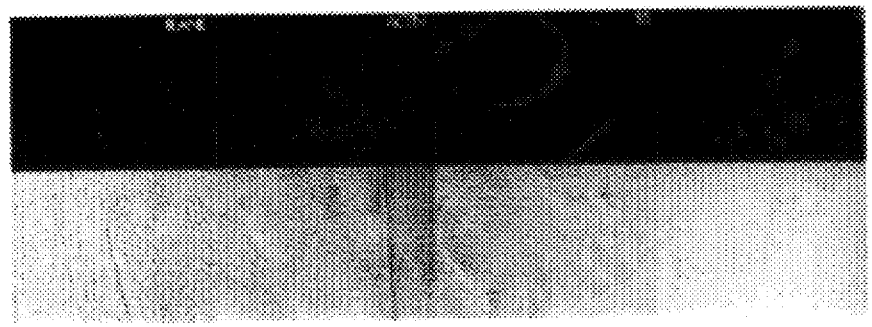
FIG. 6 demonstrates the detection of oncogenes in solid tissue samples by In Situ Hybridization.

Tissue was hybridized for 4 hours by incubation at 55° C., with a hybridization cocktail containing 50% formamide, 5× SSC, 0.1M sodium phosphate (pH 7.4) 20 mM vanadyl ribonucleoside complexes (New England Biolabs), 100 µg/ml of low molecular weight denatured herring sperm DNA, and 0.1% Octyl-phenoxy-polyethoxy-ethanol. Photobiotinylated RNA probes (prepared as described in Example 1) were added to the hybridization cocktail at a concentration of 2.5 µg/ml. No probe was added to the blank panel (FIG. 6). Hybrids were detected by adding fluorescein labelled avidin/streptavidin (A/SA) solutions directly onto the slides, and incubated for 30 minutes at room temperature. Slides were washed, coverslipped and photographed as described in Example 6.

FIG. 6 demonstrates the results of mRNA in situ hybridization and the localization of SIS/PDGF-B expression in the epithelial components of fibrocystic disease (FIG. 6, panel "SIS") and lactating adenoma (FIG. 6, panel "SIS"). In situ hybridization with a Photobiotinylated DNA probe demonstrating expression of the actin gene in the stroma as well as in the epithelial cells of fibrocystic disease (FIG. 6, panel "ACTIN"). Lower panels show comparable phase contrast microscopic features of the tissue.

EXAMPLE 8

Detection of HIV in Human Peripheral Blood

Ten ml., of human peripheral blood or 2 ml., of human bone marrow cells were incubated at 37° C., in a 1.2% ammonium oxalate solution to lyse the red blood cells. The white blood cells were centrifuged at 3,000 rpm for 10 minutes in a clinical centrifuge. The cell pellet was subsequently washed with 10 ml PBS and the pellet was resuspended in PBS. Cells were deposited by cytocentrifugation onto precleaned glass slides and air dried for 5 min. The cells were then fixed in 75% ethanol/20% acetic acid for 20 min. at room temperature.

No prehybridization step was performed. 20 ml of hybridization solution consisting of 50% formamide, 4× SSC, 0.1M sodium phosphate (pH 7.4), 0.1% Octyl-phenoxy-polyethoxy-ethanol, 100 µg/ml low molecular weight DNA (sheared herring sperm DNA obtained from Sigma Chemical Co.) and 2.5 µg/ml HIV anti-sense RNA probes labeled with Photobiotin, was added to each specimen. The antisense RNA probes were prepared as described in Example 1. After incubation for 2 hrs. at 55° C., hybrid formation was detected.

To detect hybrids, streptavidin fluorescein complex at 2× the manufacturer's recommended concentration was added to the specimen. After incubation at room temperature for 30 minutes, the specimens were then gently washed (1–200 ml per cm² of cell area) with each of the following solutions containing 0.1% Octyl-phenoxy-polyethoxy-ethanol, in order: 2× SSC, 1× SSC, 0.5× SSC, and 0.1× SSC. One drop of a 50/50 (v/v) 100% glycerol/2× PBS solution was added to each specimen. Specimens were photographed with high speed film (Kodak EES135, PS 800/1600) at 1600 ASA for 20 sec. exposure on a Nikon Photophot microscope at 400× magnification using a standard filter combination for transmission of fluorescent light.

Figure 9:
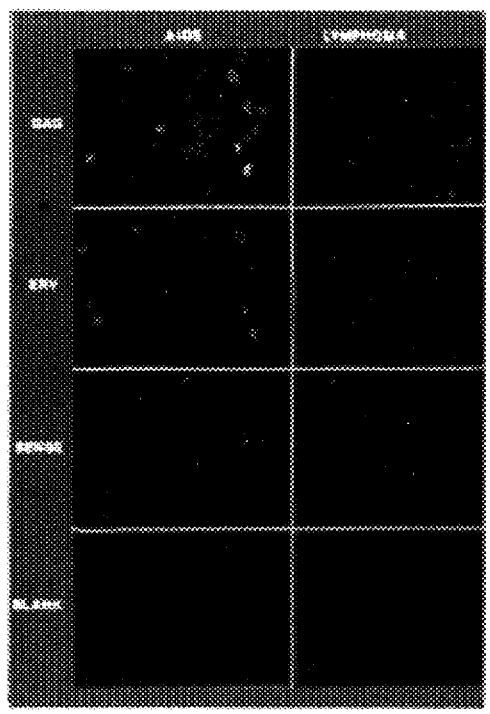
FIG. 9 demonstrates the detection of HIV in patients with Acquired Immune Deficiency Syndrome (AIDS) or Lymphoma by In Situ Hybridization.
Figure 10:
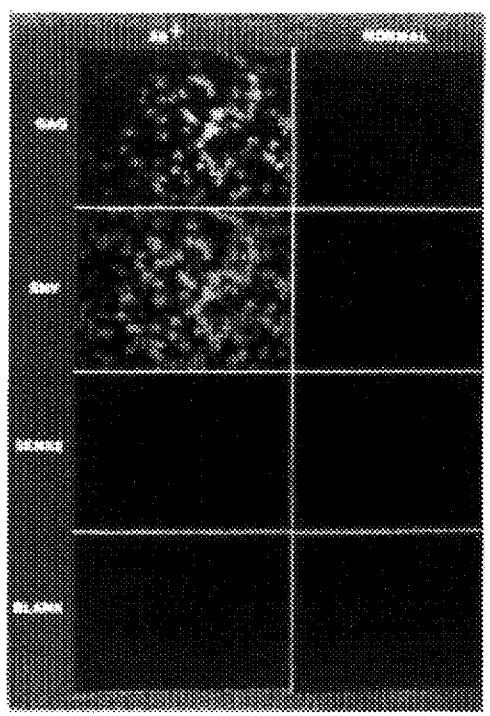
FIG. 10 demonstrates the detection of HIV in seropositive. (Ab+), asymptomatic, high risk individuals by In Situ Hybridization.

FIGS. 7–10 represent the results seen by identifying HIV in control cell lines derived from patients with AIDS or from fresh patient samples. In FIG. 7 control cell lines either infected with HIV as indicated by the plus (+) on the left hand side or a control cell line infected by HTLVI as indicated by the minus (−) on the left hand side were hybridized to four different regions of HIV: ENV, GAG, TAT or LTR genes. Unless otherwise indicated, anti-sense RNA probes were used in the hybridizations. The top four panels indicate that these four genes can readily identify HIV in infected cells. The control probes, the GAG, ENV, TAT, LTR sense probes, do not detect HIV sequences. They are correctly negative. The anti-sense RNA probes used in the top four panels to detect HIV are specific. They do not cross react with other viral sequences such as HTLVI, as indicated in the bottom two panels. FIG. 8 indicates that when the GAG and ENV probes are used to detect HIV in patients with Kaposi's Sarcoma (KS), the virus is readily identified in fresh peripheral blood. The controls which were performed on this blood, sense strand controls for these same genes and a Blank (no probe), were, as expected, negative. These same probes also identified, as shown in FIG. 8, a virus in a patient with AIDS related complex (ARC). The controls, Sense strand RNA and Blank, are negative. In FIG. 9, these same anti-sense RNA probes identified HIV in a patient with AIDS. The controls, Sense and Blank, were negative. In FIG. 10 these probes identified the presence of HIV in an asymptomatic, seropositive (Ab+) individual. The controls were negative. These probes did 5 not cross react with and did not detect HIV in uninfected normal individuals (FIG. 10).

EXAMPLE 9

Simultaneous Detection of Three mRNAs in Human Peripheral Blood

Fresh peripheral blood from a patient with chronic myelogenous leukemia in early accelerated phase was obtained by venipuncture. Red blood cells were lysed with ammonium oxalate. White blood cells were prepared and deposited onto slides as described in Example 6. After fixation, the specimens were taken through the several hybridization steps as described above in Example 6 with the following modifications: a probe for the c-sis gene was incubated with the slides for one hour using the in situ hybridization solution described in Example 5. Streptavidin-rhodamine was used to detect hybrid formation. The wash steps followed this detection, only all solutions were RNase free and contained 0.01M D-Biotin. A hybridization was repeated with a second probe for the c-myc gene; after 1 hour, the hybrids formed were detected using streptavidin-FITC. Washes were repeated as above, and a final hybridization was carried out with a probe for the c-abl gene. Hybrids formed with this probe were detected using streptavidin conjugated to alkaline phosphatase. The specimens were washed as described in Example 5 with the inclusion of 1–10 µg/ml of RNase A to each of the wash solutions. The substrates for the alkaline phosphatase (nitroblue tetrazolium and 5-bromo-4-chloro-3-indol-phosphate) were added, and the reduction of nitroblue tetrazolium was carried out for 5 minutes at room temperature.

Figure 11:
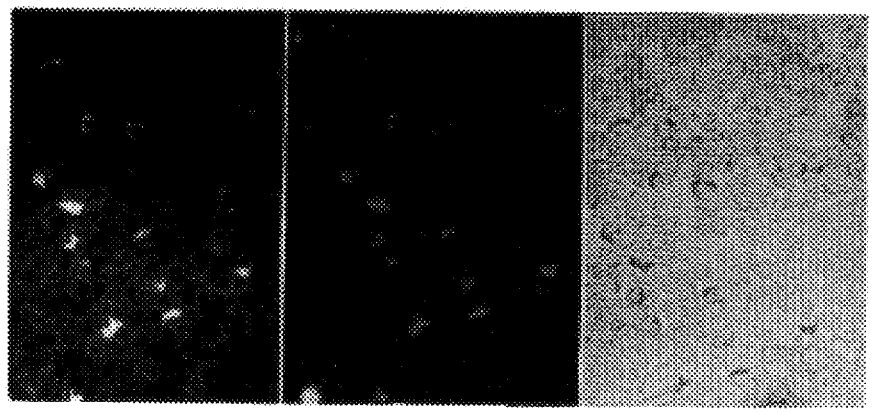
FIG. 11 demonstrates the simultaneous detection by In Situ Hybridization of three oncogenes within the same peripheral blood cells of a patient with chronic myelogenous leukemia (CML). Fluorescent and enzymatic In Situ Hybridization detections are used for the analysis.

Using this in situ hybridization technique which permitted the simultaneous detection of multiple different mRNA species, we have demonstrated that the over-expression of c-sis, c-myc and c-abl all occur within the same cells in patients' peripheral blood with chronic myelogenous leukemia. In FIG. 11, the cells containing the c-myc oncogene mRNA (MYC, the left panel) was detected by the presence of a green color emission due to the reaction of a streptavidin-fluorescein complex with the hybrids formed between the probe and target biopolymer sequences. The same cells were also shown to contain the c-sis oncogene mRNA (SIS, middle panel) by the detection of red fluorescence resulting from the presence of reacted avidin/streptavidin-rhodamine with the reacted probe. The presence of the c-abl oncogene (ABL) within the same cells is shown in the right panel by the presence of the dark blue, reacted and precipitated nitroblue tetrazolium product.

Figure 12:
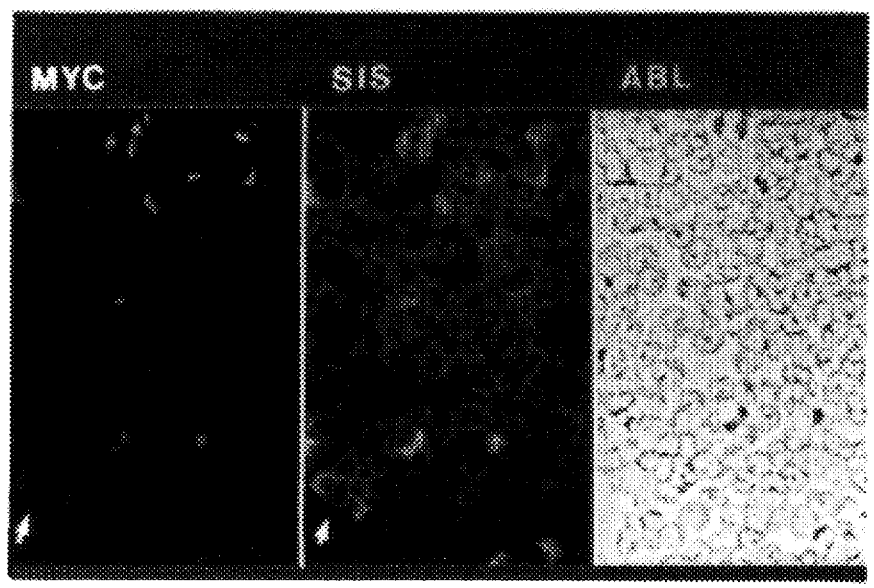
FIG. 12 demonstrates the simultaneous detection of three oncogenes within the same peripheral blood cells of a patient with chronic myelogenous leukemia (CML). Fluorescent and colloidal gold In Situ Hybridization detections are used for the analysis.

In FIG. 12, the same result is shown as in FIG. 11, only a different patient sample was used and a different detection method was employed to identify the presence of the c-abl oncogene mRNA. In this case, streptavidin labeled with colloidal gold (Bethesda Research Laboratories, catalog #9532SA; Horisberger, M. (1981) *Scanning Electron Microscopy* 11:9) was used in the detection step described above instead of streptavidin tagged with the enzyme alkaline phosphatase. No further treatments were necessary and the cells were washed as described above. The presence of black precipitate or grains seen within cells when using either bright field or phase contrast microscopy techniques, or the visualization of bright white areas of light when using either epi-polarization or dark field microscopy indicated that the cells contained target biopolymer mRNA sequences substantially complementary to the probe, in this case to the c-abl gene.

EXAMPLE 10

Detection of Nucleic Acids and Proteins in Peripheral Blood Cells

Ten ml., of human peripheral blood were incubated at 37° C., in a 1.2% ammonium oxalate solution to lyse the red blood cells. The white blood cells were centrifuged at 3,000 rpm for 10 minutes in a clinical centrifuge. The cell pellet was subsequently washed with 10 ml. PBS and the pellet was resuspended in PBS. Cells were deposited by cytocentrifugation onto precleaned glass slides and air dried for 5 min. The cells were then fixed in 75% ethanol/20% acetic acid for 20 min. at room temperature.

No prehybridization step was performed. 20 µl of hybridization solution consisting of 50% formamide, 4× SSC, 0.1M sodium phosphate (pH 7.4), 0.1% Octyl-phenoxy-polyethoxy-ethanol, 100 µg/ml low molecular weight DNA (sheared herring sperm DNA obtained from Sigma Chemical Co.) and 2.5 µg/ml of c-abl anti-sense RNA probe labelled with Photobiotin, was added to each specimen. The anti-sense RNA probe was prepared as described in Example 1. After incubation for 2 hrs. at 55° C., hybrid formation was detected.

To detect hybrids, streptavidin-rhodamine complex at 2× the manufacturer's recommended concentration was added to the specimen. During this incubation, rabbit polyclonal antibody raised against the c-abl gene product (supplied by Dr. Russel Grieg of Smith Kline & French, Swedeland, Penn.) was added to the specimen at a concentration which positively labeled K562 cells and did not show any detectable signal in HL60 cells when a fluorescein labeled anti-rabbit IgG was added.

After incubation at room temperature for 30 minutes, the specimens were then gently washed (1–200 ml per cm² of cell area) with each of the following solutions containing 0.1% Octyl-phenoxy-polyethoxy-ethanol, in order: 2× SSC, 1× SSC, 0.5× SSC, and 0.1× SSC. One drop of a 50/50 (v/v) 100% glycerol/2× PBS solution was added to each specimen. Specimens were photographed with high speed film (Kodak EES135, PS 800/1600) at 1600 ASA for 20 sec. exposure on a Nikon Photophot microscope at 400× magnification using a standard filter combination for transmission of fluorescent light.

Figure 13A:
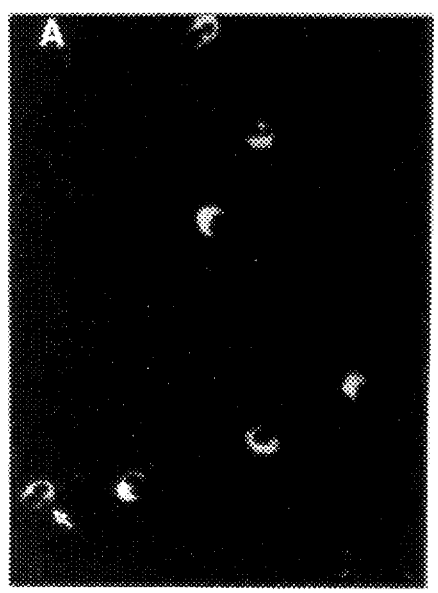
FIG. 13A and B demonstrate the simultaneous detection of antigens and nucleic acids within the same cells using In Situ Hybridization.
Figure 13B:
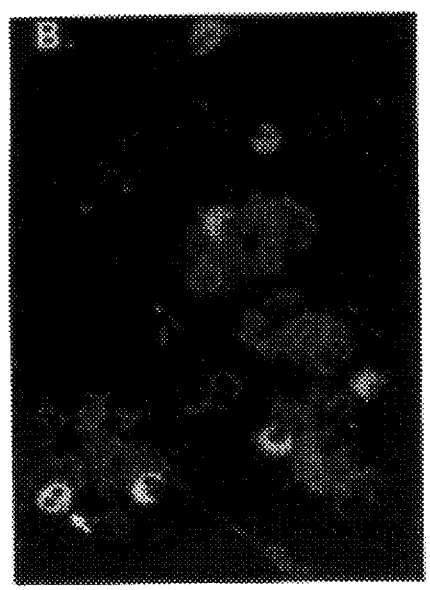

It is known that c-abl mRNA and protein are over-produced within the same cell in patients with chronic myelogenous leukemia (CML) (Sram, K. et al. (1985) *N. Engl. J. Med.* 313:1429; Konopka, J. B. and Witte, O. N. (1984) *Cell* 37:3116). Using the present invention, peripheral blood cells from a patient with CML were probed for the presence of mRNA corresponding to the c-abl gene and simultaneously, as described above, for the presence of the c-abl protein product. FIG. 13 A demonstrates that the protein was readily detectable due to the fluorescein fluorescence emission of the reacted antibodies. In the same cells, FIG. 13 B shows the presence of the c-abl mRNA, detectable due to the rhodamine fluorescence emission.

EXAMPLE 11

Quantitation of the Number of Target Biopolymer Molecules

K562 Cells (ATCC #CCL 243) were grown in Hank's Balanced Salts Solution supplemented with 10% Fetal Calf Serum. Three days after the last change in media, the cells were split to a density of about $10^5$ cells per 0.3 ml., of fresh media. One hour later, 60 replica slides were made by depositing 50,000–100,000 cells onto a slide by cytocentrifugation. The remainder of the cells were harvested and RNA and DNA was extracted from the cells by the guanidinium cesium chloride method (Chirgwin, et al. (1979) *Biochemistry* 18:5294).

Since the cell line was a relatively homogeneous population, the extracted RNA was purified and used to determine copy number estimates for each RNA species analyzed; i.e., an estimate could be made of the number of molecules of each gene present within each cell from a series of control experiments well known to those with knowledge and skill in the art. These control experiments to determine the number of molecules per cell included the following: Northern blots, RNA dot blots, Quick-blots, Cytodots, single copy saturation experiments, and solution concentration versus time hybridization experiments (Rot$_{1/2}$ m analysis) (Hames, B. D. and Higgins, S. J. (1986) in *Nucleic Acid Hybridization: a practical approach*, IRL Press, Oxford-Washington, D.C.).

Cells on slides were fixed with 75% ethanol/20% glacial acetic acid/5% water for 20 minutes at room temperature.

No prehybridization step was performed. 20 μl of hybridization solution consisting of 50% formamide, 4× SSC, 0.1M sodium phosphate (pH 7.4), 0.1% Octyl-phenoxy-polyethoxy-ethanol, 100 μg/ml low molecular weight DNA (sheared herring sperm DNA obtained from Sigma Chemical Co.) and 2.5 μg/ml of an anti-sense RNA probe labelled with Photobiotin, was added to each specimen. Probes used were either the sense or anti-sense RNA strands the following genes: c-abl, c-sis, c-myc, or Epstein Barr Virus (EBV). The probes were prepared as described in Example 1. After incubation for 2 hours at 55° C., hybrid formation was detected.

To detect hybrids, streptavidin-fluorescein (SA-FITC), streptavidin-phycoerythrin (SA-PE), streptavidin-rhodamine B(SA-R), streptavidin-Texas Red (SA-TR), streptavidin-phycocyanin (SA-PC), or streptavidin-allophycocyanin (SA-APC) complexes were added at 2× the manufacturer's recommended concentration. (SA-FITC, SA-TR: Bethesda Research Laboratories; SA-R: Southen Biologicals; SA-PE, SA-PC, SA-APC: BioMeada). After incubation at 37° C., for 10 minutes, the specimens were then gently washed with (1–200 ml. per cm$^2$ of cell area) with 0.1× SSC containing 0.1% Octyl-phenoxy-polyethoxy-ethanol. One drop of a 50/50 (v/v) 100% glycerol/2×PBS solution was added to each specimen and a #1 coverslip was placed over the cells before microscopic examination.

Fluorescence emitted from each cell is a reflection of the number of streptavidin molecules which reacted with probe; the amount of reacted probe within a cell is indicative of the number of target biopolymers present within the cell. To measure the fluorescence within each cell, slides were analyzed using the ACAS 470 Workstation from Meridian Instruments (Okemos, Mich.). The Meridian instrument, like most image processing systems, excites the fluors present within a sample and then captures the emitted light as either a digital or analog signal. This signal is digital on the Meridian instrument. The quantity of the signal can be represented by different colors.

Figure 14:
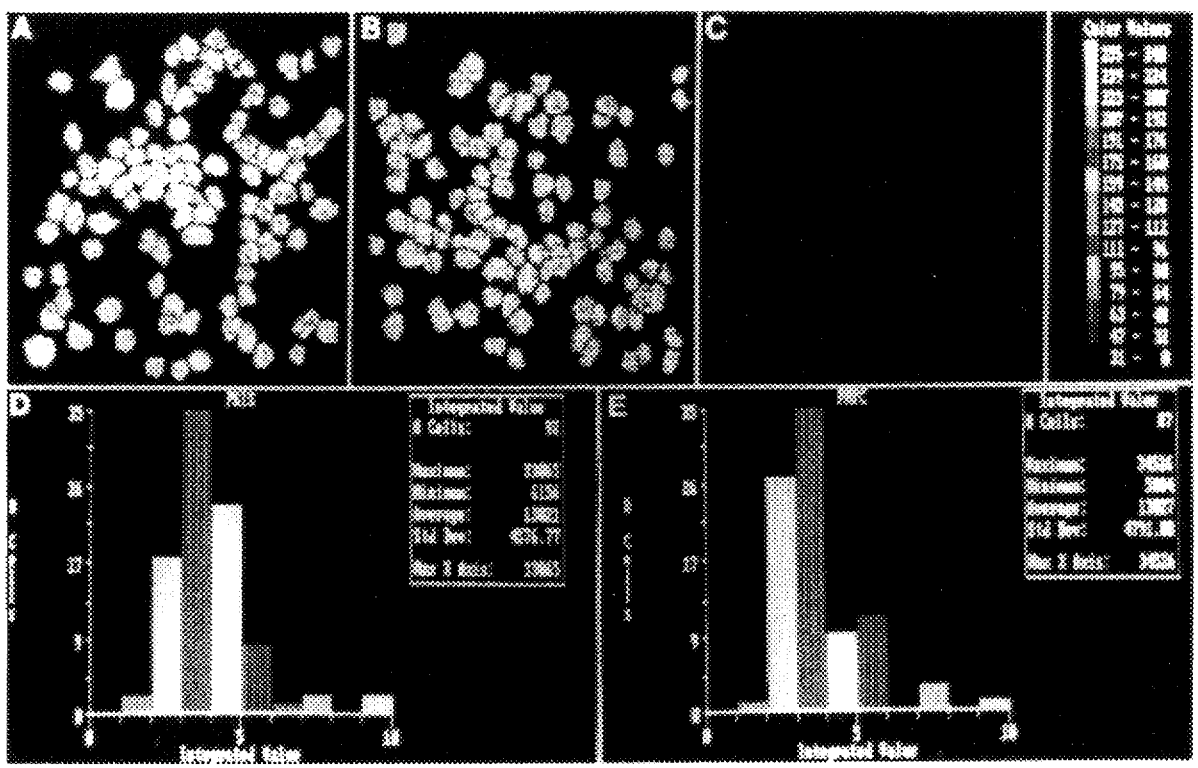
FIG. 14(A-E) demonstrate a quantitative analysis of In Situ Hybridization data.

In FIG. 14, this is illustrated in the top right hand panel which shows the colors the instrument assigns to emitted signals of different intensities. When these colors are represented over a cell (FIGS. 14 A–C), the relative amount of emitted fluorescence per cell can be seen. In FIG. 14A shows the detection of the c-sis gene; the intensity of emission of reacted fluorescer is seen; in FIG. 14B, the detection of c-myc is shown. FIG. 14C shows the background signal emitted when no probe is included in the hybridization solution. This panel is a negative control and is blank. The Meridian instrument can determine the total fluorescence over the entire cell (i.e., quantity of fluorescence per cell) and represent this information graphically. The control experiments described above which were carried out with purified RNA from other cells showed that both the c-sis and c-myc cellular target genes were present in these cells at between 1 and 10 molecules per cell. Therefore, this value represents the scale on the horizontal axis in FIG. 14D and 14E. The present invention together with the appropriate instrumentation, was capable of identifying the number of cells which contained even a single molecule of either the c-sis or c-myc gene.

EXAMPLE 12

Error Rates of the In Situ Hybridization System

K562 Cells (ATCC #CCL 243) were grown in Hank's Balanced Salts Solution supplemented with 10% fetal calf serum. Three days after the last change in media, the cells were split to a density of about 10$^5$ cells per 0.3 ml of fresh media. One hour later, 60 replica slides were made by depositing 50,000–100,000 cells onto a slide by cytocentrifugation. The remainder of the cells were harvested and RNA and DNA was extracted from the cells by the guanidinium cesium chloride method as in the previous Example 11.

Since the cell line was a relatively homogeneous population, the extracted RNA was purified and used to determine copy number estimates for each RNA species analyzed; i.e., an estimate could be made of the number of molecules of each gene present within each cell from a series of control experiments well known to those with knowledge and skill in the art. These control experiments to determine the number of molecules per cell included the following: Northern blots, RNA dot blots, Quick-blots, Cytodots, single copy saturation experiments, and solution concentration versus time hybridization experiments (Rot$_{1/2}$ analysis) (Hames, B. D. and Higgins, S. J. (1986) in *Nucleic Acid Hybridization: a practical approach*. IRL Press, Oxford-Washington, D.C.).

Cells on slides were fixed with 75% ethanol/20% glacial acetic acid/5% water for 20 minutes at room temperature.

No prehybridization step was performed. 20 μl of hybridization solution consisting of 50% formamide, 4× SSC, 0.1M sodium phosphate (pH 7.4), 0.1% Octyl-phenoxy-polyethoxy-ethanol, 100 μg/ml low molecular weight DNA (sheared herring sperm DNA obtained form Sigma Chemical Co.) and 2.5 μg/ml of an anti-sense RNA probe labeled with Photobiotin, was added to each specimen. Probes used were either the sense or anti-sense RNA strands of the following genes: c-abl, c-sis, c-mvc, or Epstein Barr Virus (EBV). The probes were prepared as described in Example 1. After incubation for 2 hours at 55° C., hybrid formation was detected.

To detect hybrids, streptavidin-fluorescein (SA-FITC), streptavidin-phycoerythrin (SA-PE), streptavidin-rhodamine B (SA-R), streptavidin-Texas Red (SA-TR), streptavidin-phycocyanin (SA-PC), streptavidin-allophycocyanin (SA-APC) complexes were added at 2× the manufacturer's recommended concentration. (SA-FITC, SA-TR: Bethesda Research Laboratories; SA-R: Southen Biologicals; SA-PE, SA-AP: BioMeada). After incubation at 37° C. for 10 minutes, the specimens were then gently washed (1–200 ml per cm of cell area) with 0.1× SSC containing 0.1% Octyl-phenoxy-polyethoxy-ethanol. One drop of a 50/50 (v/v) 100% glycerol/2× PBS solution was added to each specimen and a #1 coverslip was placed over the cells before microscopic examination.

Fluorescence emitted from each cell is a reflection of the number of streptavidin molecules which reacted with probe; the amount of reacted probe within a cell is indicative of the number of target biopolymers present within the cell. To measure the fluorescence within each cell, slides were analyzed using the ACAS 470 Workstation from Meridian Instruments (Okemos, Mich.). The Meridian instrument, like most image processing systems, excites the fluors present within a sample and then captures the emitted light as either a digital or analog signal. This signal is digital on the Meridian instrument. In a manner similar to the method described in Example 11, the total fluorescence per cell was determined using the ACAS 470 workstation. The data obtained was then analyzed by the Mann-Whitney test to determine if there were statistically significant differences between the amounts of fluorescence seen when different probes were used in the in situ hybridization system.

In a cell line which has a known target biopolymer RNA present, a probe should react with the target; this would lead to the generation of a fluorescent signal within the positive cells. In cases in which the "target" biopolymer RNA is known to be absent from the cells, a probe reactive to the target should not bind in any non-specific manner to the cells and thus should not generate any fluorescent signal within the cells. A statistical test can determine whether this is true and whether the difference between the "positive" and the "negative" is sufficiently different to be correct and not random. Furthermore, the statistical test can determine the probability of the test incorrectly identifying a negative sample as positive or a positive sample as negative. Table 1 shows the results of this statistical analysis. The positive samples were correctly identified. The error rates represent the chance of obtaining false results when different thresholds of sensitivity for the present invention are employed.

TABLE 1

In Situ Hybridization: False Positive, False Negative Rates

| Detection Threshold | Error Rate |
| --- | --- |
| 1-2 genes/cell | 1.71% |
| 1-5 genes/cell | 0.65% |
| >10 genes/cell | >0.005% |

EXAMPLE 13

Detection of Cytomegalovirus in Peripheral Blood

One ml. of human peripheral blood was obtained from the patients described in Example 8 and processed as described in that Example. The hybridization reaction was carried out with the specimens using the same hybridization cocktail described in Example 4, except the probe was an anti-sense RNA probe complementary to cytomegalovirus (CMV) RNA and labeled with Photobiotin. Hybrid detection was carried out as described in Example 8.

Figure 15:
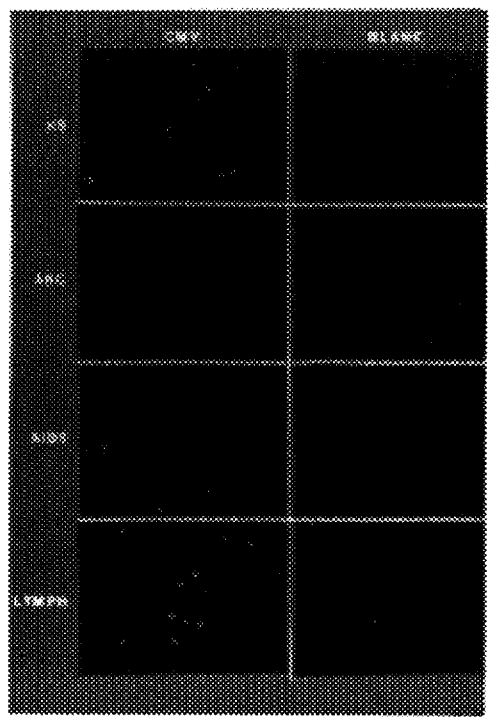
FIG. 15 demonstrates the detection of Cytomegalovirus (CMV) in patients with Kaposi's Sarcoma (KS), AIDS Related Complex (ARC), Acquired Immune Deficiency Syndrome (AIDS), or Lymphoma.
Figure 16:
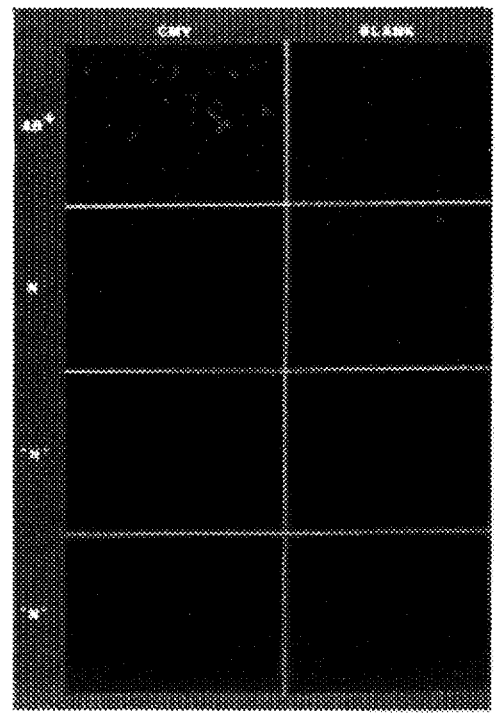
FIG. 16 demonstrates the detection of Cytomegalovirus (CMV) in seropositive (Ab+), asymptomatic, high risk individuals by In Situ Hybridization.

The column of photomicrographs in FIGS. 15 and 16 on the left (CMV) illustrates that the present invention is capable of detecting target viral biopolymers—here detecting CMV—within a specimen. The presence of CMV in the specimen is indicated by the emitted light within the cells. The column of photomicrographs in FIGS. 15 and 16 on the right (BLANK) shows no emitted light; these pictures show that in the controls no extraneous signals were produced.

EXAMPLE 14

Figure 17:
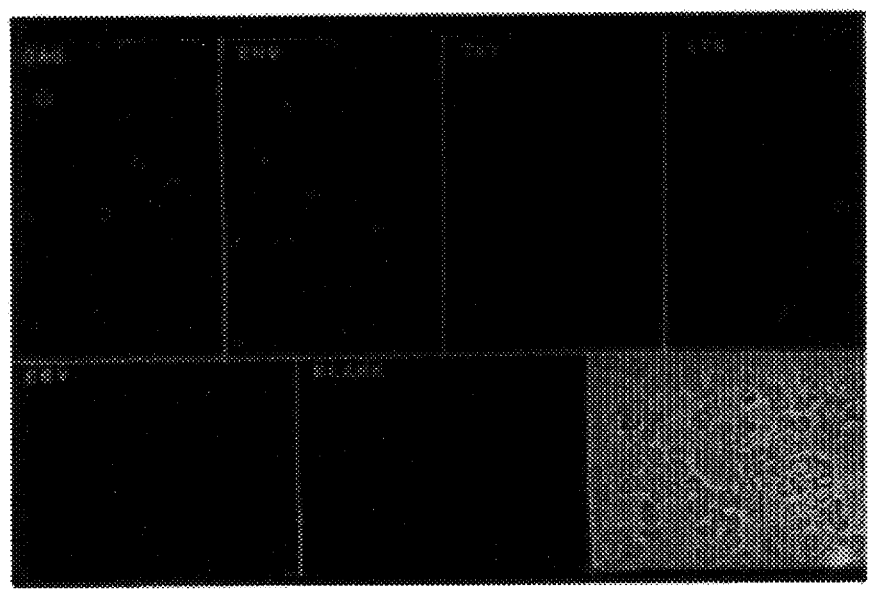
FIG. 17 demonstrates the detection by In Situ Hybridization of four different portions of HIV (GAG, ENV, TAT, LTR) in a person who is at risk for viral infection but tests seronegative for HIV.
Figure 18:
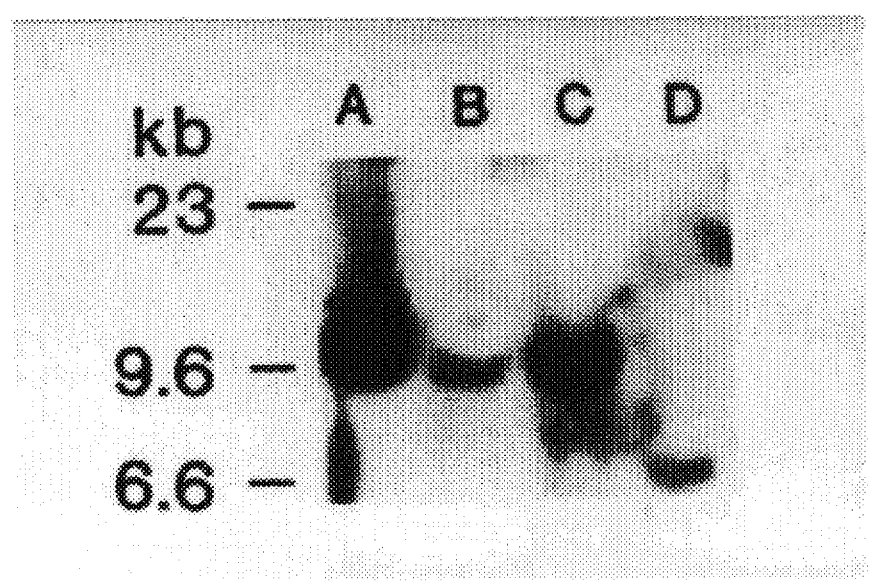
FIG. 18 demonstrates the confirmation of the In Situ Hybridization results in FIG. 17 by a Southern Blot assay.

Detection of HIV in Peripheral Blood Cells of an Individual Seronegative for HIV but at High Risk for HIV Infection Ten ml. of human peripheral blood from an individual at high risk for HIV infection was obtained, processed, hybridized and hybrids detected and photographed as described in Example 8. In FIG. 17, the panels marked GAG, ENV, TAT, LTR, EBV represent results obtained when the corresponding anti-sense RNA probes were added to the hybrid solution. The panels with HIV anti-sense probes added are positive while EBV is negative. The panel marked "Blank" represents results obtained when no probe was added to the hybrid solution and is negative. The bottom right panel is a phase contrast photomicrograph of the cells in the panel marked "Blank".

To confirm that HIV was present in the blood cells of this individual, a Southern blot analysis (Southern, (1975) *J. Mol. Biol.* 98:503) of DNA from the HIV infected cell line H-9 (ATCC #CRL 8543) (lanes A and C) and from the peripheral blood cells from this same seronegative but high risk individual (lanes B and D) is presented in FIG. 19. DNA in lanes A and B was digested with SstI and in lanes C and D with HindIII. The blot was hybridized with a full length HW probe, radiolabeled with $^{32}P$, and demonstrates that HIV hybridizing sequences are present in the peripheral blood cells of this individual.

EXAMPLE 15

Usefulness of In Situ Hybridization to Monitor Effectiveness of Patient Therapy

Figure 19:
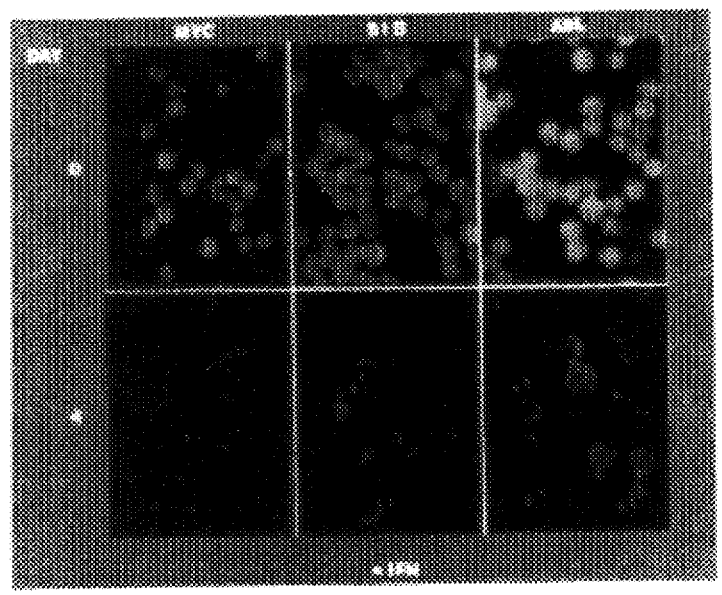
FIG. 19 demonstrates the ability to monitor the results of alpha-interferon therapy in patients by In Situ Hybridization.
Figure 20:
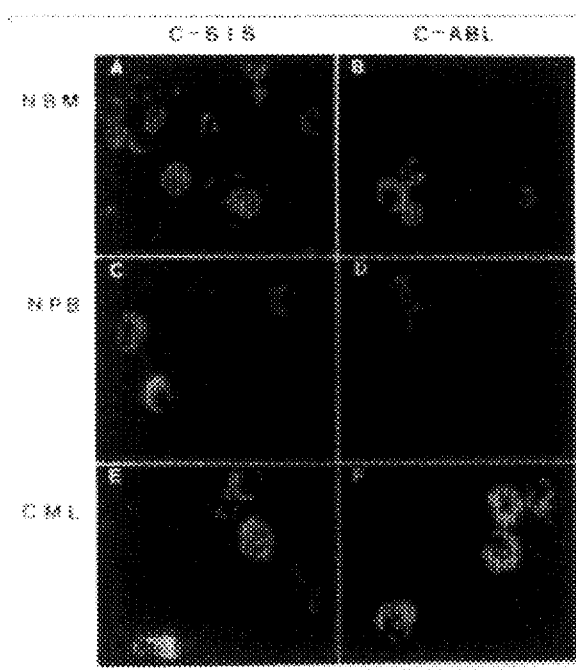
FIG. 20 demonstrates the ability to monitor the results of gsmma-interferon therapy in patients by In Situ Hybridization.

Peripheral blood was obtained from patients with chronic myelogenous leukemia (CML) both before and after treatment with either alpha or gamma interferon. The blood was processed, hybridization was accomplished, and hybrids were detected as described in Example 6. FIG. 19 demonstrates that in a CML patient before alpha-interferon treatment (Day 0) the c-myc, c-sis, and c-abl oncogene target biopolymers were all present, as demonstrated by the light emitted from the cells and seen on the photomicrographs at day 0. In the same patient, the same target cellular genes were not produced after four days of alpha-interferon therapy (little or no signal is seen in the cells at day 4). In contrast, in a patient who underwent treatment with gamma-interferon, cells were still present which over-produced the c-sis and c-abl oncogene (FIG. 20, Panels E and F). Clinically, the patient who was treated with alpha-interferon responded well to the therapy and went into remission. The patient who received gamma-interferon failed to respond to this therapy. The monitoring of changes in the type or amount of a cellular target biopolymer sequence may be an important means of evaluating or predicting the effectiveness of therapeutics.

One skilled in the art will readily appreciate that the present invention is well adapted to carry out the objects and obtain the ends and advantages mentioned, as well as those inherent therein. The components, methods, procedures and techniques described herein are presently representative of the preferred embodiments, are intended to be exemplary, and are not intended as limitations on the scope of the present invention. Changes therein and other uses will occur to those skilled in the art which are encompassed within the spirit of the invention and are defined by the scope of the appended claims.

What is claimed is:

1. A method for assaying target polynucleotides in a cellular specimen, said method comprising the steps of:

contacting a cellular specimen with a fixation medium to yield a fixed specimen having therein cells with substantially intact membranes, said fixation medium comprising at least one agent that is a precipitating agent or a cross-linking agent, said agent being an agent that allows double-stranded cellular polynucleotides to shift under hybridizing conditions to about 70% single-stranded cellular polynucleotides while maintaining cellular spatial relationships;

incubating said fixed specimen with a hybridization solution comprising a denaturing agent, a hybrid stabilizing agent, a buffering agent, a membrane pore-forming agent and at least one probe having a nucleotide sequence at least substantially complementary to a specific target nucleotide sequence to be detected, said incubating being under hybridizing conditions so that double-stranded cellular polynucleotides shift to about 70% single-stranded cellular polynucleotides, and detecting duplexes formed between said probe and said specific target nucleotide sequence in said cells with substantially intact membranes;

wherein the time for performing said steps of contacting, incubating, and detecting does not exceed a total of about 4 hours;

whereby target polynucleotides are assayed in a cellular specimen;

wherein said shift under hybridizing conditions to about 70% single-stranded cellular polynucleotides while maintaining celluar spatial relationships is determinable by a process comprising the following four steps:
 (a) staining cells with a stain able to stain polynucleotides within said cells to yield a different emission spectnun upon ultraviolet excitation of stained double-stranded and stained single-stranded polynucleotides;
 (b) determining the total mount of emitted fluorescence of a cell sample not treated under hybridizing conditions;
 (c) determining the total amount of emitted fluorescence of cell samples treated by various fixation and hybridization procedures and times;
 (d) assessing when the nmount of fluorescence corresponding to the amount of double-stranded polynucleotide has decreased about 70%.

2. The method of claim 1, wherein:
probes having nucleotide sequences at least substantially complementary to specific target nucleotide sequences to be detected are used at a concentration of at least 1.0 microgram per milliliter hybridization solution, and said method is capable of detecting as few as five copies of said target nucleotide sequence per cell.

3. The method of claim 2, comprising an additional step of:
quantitating said detection of duplexes formed between said probe and said target nucleotide sequence.

4. The method of claim 3, wherein:
said quantitating comprises:
determining the quantity of said duplexes formed between said probe and said target nucleotide sequence detected in one or more cells of said cellular specimen, or determining the quantity of said cells of said cellular specimen, wherein said duplexes between said probe and said target nucleotide sequence are detected.

5. The method of claim 1, wherein said step of detecting duplexes is accomplished by means of a detectable label attached to said probe.

6. The method of claim 1, wherein said step of detecting duplexes is accomplished by means of a detectable label which is added after formation of said duplexes is complete.

7. The method of claim 1, wherein said detectable label is selected from the group consisting of: radioactive labels, fluorescers, chemiluminescers, and enzyme labels.

8. The method of claim 1, wherein said detectable label is selected from avidin or streptavidin.

9. The method of claim 1, wherein said precipitating agent is selected from the group consisting of: ethanol, methanol, acetone, combinations thereof, and combinations of any of the foregoing with formaldehyde.

10. The method of claim 1, wherein said cross-linking agent is selected from the group consisting of: paraformaldehyde, formaldehyde, dimethylsuberimidate and ethyl-dimethylamino-propylcarbodiimide.

11. The method of claim 1, wherein said denaturing agent is selected from the group consisting of: formamide, urea, sodium iodide, thiocyanate, guanidine, perchlorate, trichloroacetate and tetramethylamine.

12. The method of claim 11, wherein said denaturing agent is formamide.

13. The method of claim 12, wherein said denaturing agent is formamide at a concentration of 20% to 80%.

14. The method of claim 1, wherein said hybrid stabilizing agent is selected from the group consisting of: sodium chloride, lithium chloride, magnesium chloride and ferric sulfate.

15. The method of claim 1, wherein said pore-forming agent is a selective pore-forming agent.

16. The method of claim 1, wherein said pore-forming agent is selected from the group consisting of: polyoxyethylene(23) lauryl ether, polyoxyethylene(20) cetyl ether, 3-((3-cholamidopropyl)-dimethylammonio)-1-propanesulphonate, octylphenoxypolyethoxyethanol, sodium deoxycholate and sodium dodecyl sulfate.

17. The method of claim 1, wherein said hybridization is-carried out at a temperature from 15° C. to 80° C.

18. The method of claim 17, wherein said temperature is from 50° C. to 55° C.

19. The method of claim 1, wherein the formamide concentration is 50% and the NaCl concentration is 0.75M.

20. The method of claim 1, wherein the formamide concentration is 50%, the NaCl concentration is 0.75M, and the sodium citrate concentration is 0.075M.

21. The method of claim 1, wherein said method is capable of detecting 1 to 5 RNA or DNA molecules per cell.

22. A method for assaying target biopolymers in a celluar specimen, said method comprising the steps of:
contacting a cellular specimen with a fixation medium comprising at least one agent that is a precipitating agent or a cross linking agent to yield a fixed spedmen having therein cells with substantially intact membranes;

incubating said fixed Specimen with a hybridization solution comprising a denaturing agent, a hybrid stabilizing agent, a buffering agent, a membrane pore-forming agent and at least two probes each specific for different target biopolymers to be detected with each such probe having a detectable label, said incubating being under hybridizing conditions for not less than five minutes so that cellular polynucleotides of said cellular specimen have shifted to about 70% single-strandedness, wherein each detectable label is selected to be distinguishable from each other detectable label; and detectingduplexes formed between each said probe and each said different target biopolymer in said cells with substantially intact membranes by means of said detectable labels;

wherein at least two target biopolymers are simultaneously assayed in a cell of the cellular specimen, and wherein the time for performing said steps of contacting, incubating, and detecting does not exceed about four hours;

whereby said target biopolymers are detected in cells of said cellular specimen;

wherein said shift under hybridizing conditions to about 70% single-stranded cellular polynucleotides while maintaing cellular spatial relationships is deteminable by a process comprising the following four steps:
   (a) staining cells with a stain able to stain polynucleotides within said cells to yield a different emission spectrum upon ultraviolet excitation of stained double-stranded and stained single-stranded polynucleotides;
   (b) determining the total amount of emitted fluorescence of a cell sample not treated under hybridizing conditions;
   (c) determining the total amount of emitted fluorescence of cell samples treated by various fixation and hybridization procedures and times;
   (d) assessing when the nmottnt of fluorescence corresponding to the amount of double-stranded nucleic acid has decreased about 70%.

23. The method of claim 22, wherein:
said target biopolymers comprise:
   a target nucleotide sequence, and
   a target biopolymer that is not a nucleotide sequence; and wherein;
said probes specific for different target biopolymers to be detected and each bearing a detectable label comprise:
   at least one first probe having a nucleotide sequence at least substantially complementary to a specific target nucleotide sequence to be detected, and
   at least one second probe having specificity for a target biopolymer that is not a nucleotide sequence;
detecting duplexes formed between said first probe and said target nucleotide sequence and duplexes formed between said second probe and said target biopolymer that is not a polynucleotide by means of said detectable labels;
wherein a target nucleotide sequence and a target biopolymer that is not a polynucleotide are simultaneously assayed in a cell of said fixed cellular specimen, and
wherein said contacting said fixed cellular specimen, said incubating and said detecting is done within four hours.

24. The method of claim 22, wherein said detectable labels are directly detectable labels.

25. The method of claim 22, wherein said step of detecting duplexes is accomplished by means of detectable labels which are added after fomation of duplexes is complete.

26. The method of claim 22, wherein said detectable labels are selected from the group consisting of: radioactive labels, fluorescers, chemilnminescers, and enzyme labels.

27. The method of claim 22, wherein one of said detectable labels is selected from avidin or streptavidin.

28. The method of claim 22, wherein said precipitating agent is selected from the group consisting of: ethanol, methanol, acetone, combinations thereof, and combinations of any of the foregoing with formaldehyde.

29. The method of claim 22, wherein said cross-linking agent is selected from the group consisting of: paraformaldehyde, formaldehyde, dimethylsuberimidate and ethyl-dimethylamino-propylcarbodimide.

30. The method of claim 22, wherein said denaturing agent is selected from the group consisting of: formarmide, urea, sodium iodide, thiocyanate, guanidine, perchlorate, trichloroacetate and tetramethylamine.

31. The method of claim 30, wherein said denaturing agent is formamide.

32. The method of claim 31, wherein said denaturing agent is formamide at a concentration of 20% to 80%.

33. The method of claim 22, wherein said hybrid stabilizing agent is selected from the group consisting of: sodium chloride, lithium chloride, magnesium chloride and ferric sulfate.

34. The method of claim 22, wherein said pore-forming agent is a selective pore-forming agent.

35. The method of claim 22, wherein said pore-forming agent is selected from the group consisting of: polyoxyethylene(23) lauryl ether, polyoxyethylene(20) cetyl ether, 3-((3-cholamidopropyl)-dimethyl amoniuo)-1-propanesulphonate, octylphenoxypolyethoxyethanol, sodium deoxycholate and sodium dodecyl sulfate.

36. The method of claim 22, wherein said hybridization is carried out at a temperature from 15° C. to 80° C.

37. The method of claim 36, wherein said temperature is from 50° C. to 55° C.

38. The method of claim 22, wherein the formamide concentration is 50% and the NaCl concentration is 0.75M.

39. The method of claim 22, wherein the formamide concentration is 50%, the NaCl concentration is 0.75M, and the sodium citrate concentration is 0.075M.

40. The method of claim 22, wherein said method is capable of detecting 1 to 5 molecules of a first target biopolymer per cell and 1 to 5 molecules of a second target biopolymer per cell.

41. A method of for assaying target polynucleotides in peripheral blood or bone marrow cells, said method comprising the steps of:
   depositing a specimen of blood or bone marrow on a solid support;
   contacting a cellular specimen with a fixation medium to yield a fixed specimen having therein cells with substantially intact membranes, said fixation medium comprising at least one agent that is a precipitating agent or a cross-linking agent, said agent being an agent that allows double-stranded cellular polynucleotides to shift unnder hybridizing conditions to about 70% single-stranded cellular polynucleotides while maintaining cellular spatial relationships;
   incubating said fixed specimen with a hybridization solution comprising about 20% to 80% formnmide, about 5 times concentrated SSC, about 0.1M tris (hydroxymethyl)aminomethane-HCl , pH 7.4, about 0.1% of octylphenoxypolyethoxyethanol and a photo-biotinylated single-stranded anti-sense RNA probe having 75–150 bases at least substantially complementary to a specific target nucleotide sequence to be detected said incubating being under hybridizing conditions so that double-strained cellular polynucleotides shift to about 70% single-stainded cellular polynucleotide, and
   adding an agent selected from avidin and streptavidin bearing a detectable label, said agent being at a concentration sufficient to bind said agent to said hybridized probe within a at least five minutes to form a probe-bound agent;
   washing said labeled specimen with a solution containing 0.1% octylphenoxypolyethoxyethanol to remove unbound agent; and
   detecing probe-bound agent in said cells with substantially intact membranes;
   wherein said shift under hybridizing conditions to about 70% single-stranded cellular polynucleotides while maintaining cellular spatial relationships is determinable by a process comprising the following four steps:

(a) staining cells with a stain able to stain polynucleotides within said cells to yield a different emission spectrum upon ultraviolet excitation of stained double-straned and stained single-stranded polynucleotides;

(b) determing the total amount of emitted fluorescence of a cell sample not treated under hybridizing conditions;

(c) determining the total amount of emitted fluorescence of cell samples treated by various fixation and hybridization procedures and times;

(d) assessing when the amount of fluorescence corresponding to the amount of double-stranded polynucleotides has decreased about 70%.

42. The method of claim 41, wherein said target polynucleotide is an oncogene.

43. The method of claim 41, wherein said target polynucleotide is a viral gene.

44. The method of claim 41, wherein said probe comprises a mixture of different probes, each to a different region of said target polynucleotide.

45. The method of claim 41, wherein said method is accomplished within about 4 hours.

46. The method of claim 41, wherein said detecting of said bound detectable label is quantitative.

47. A method for assaying a target polynucleotide in tissue specimens, said method comprising the steps of:

depositing a tissue specimen on a solid support;

contacting said tissue specimen with a fixation medium to yield a fixed specimen having therein cells with substantially intact membranes while maintaining cellular spatial relationships;

wherein said contacting is performed for at least 20 minutes at a temperature from −20° C. to 50° C., wherein said fixation medium comprises 50% methanol/50% acetone, so as to allow about a 70% shift of double-stranded to single-stranded cellular polynucleotides;

incubating said fixed specimen with a hybridization solution comprising about 20% to 80% formamide, about 5 times concentrated SSC, about 0.1M sodium phosphate, pH 7.4, about 0.1% of octylphenoxypolyethoxyethanol, 20 mM vanadyl ribonucleoside complexes, a photobiotinylated single-stranded anti-sense RNA probe having 75–160 bases at least substantially complementary to a specific target nucleotide sequence to be detected, and low molecular weight denatured DNA at a concentration 100 times greater than the probe concentration said incubating being under hybridizing conditions so that the double-stranded cellular polynucleotides have shifted to about 70% single-strandedness, and adding a detectably labeled agent selected from avidin and streptavidin at a concentration sufficient to bind to duplexes formed between said probe and said target polynucleotide within at least 5 min to form bound detectably labeled agent;

washing said labeled specimen with a solution containing 0.1% octylphenoxypolyethoxyethanol to remove unbound detectably labeled agent; and detecting said bound detectably labeled agent in said cells having substantially intact membranes, wherein:

said shift under hybridizing conditions to about 70% single-stranded cellular polyucleotides while maiutnining cellular spatial relationships is determinable by a process comprising the following four steps:

(a) staining cells with a stain able to stain polynucleotides within said cells to yield a different emission spectrum upon ultraviolet excitation of stained double-stranded and stained single-stranded polvnucleotides;

(b) determining the total amount of emitted fluorescence of a cell sample not treated under hybridizing conditions;

(c) determining the total mount of emitted fluorescence of cell snmples treated by various fixation and hybridization procedures and times;

(d) assessing when the amount of fluorescence corresponding to the amount of double-stranded nucleic acid has decreased about 70%.

48. The method of claim 47, wherein said target polynucleotide is an oncogene.

49. The method of claim 47, wherein said target polynucleotide is a viral gene.

50. The method of claim 47, wherein said probe comprises a mixture of different probes, each to a different region of said target pelynucleotide.

51. The method of claim 47, wherein said method is accomplished within about 4 hours.

52. The method of claim 47, wherein said detecting of said detectable label is quantitative.

53. The method of claim 2, wherein said method is capable of detecting as few as one copy of said target nucleotide sequence per cell.

54. A method for selection of a fixative and determination of the optimum hybridization conditions for conducting an assay for a target polynucleotide in a cellular specimen, said assay comprising the steps of:

(A) contacting a cellular specimen with a fixation medium to yield a fixed specimen having therein cells with substantially intact membranes, said fixation medium compriagent or a cross-linking agent, said precpitating agent or a cross-linking agent, said agent being an agent that allows double-stranded cellular polynucleotides to shift under hybridizing conditions to about 70% single-stranded cellular polynucleotides while maintaining cellular spatial relationships;

(B) incubating said fixed specimen with a hybriclization solution comprising a denaturing agent, a hybrid stabilizing agent, a buffering agent, a membrane pore-forming agent and at least one probe having a nucleotide sequence at least substantially complementary to a specific target nucleotide sequence to be detected, said incubating being under hybridizing conditions so that double-stranded cellular polynucleotides skift to about 70% single-stranded cellular polynucleotides, and (C) detecting duplexes formed between said probe and said specific target nucleotide sequence in said cells with substantially intact membranes;

wherein said method is capable of detecting as few as five polynucleotide molecules per cell;

wherein selection of a fixstive comprises the steps of:

(a) harvesting cells from a specimen;

(b) applying a fixative;

(c) incubating said cells with said fixative;

(d) comparing the degree of preservation of cellular morphology after fixation to the morphology prior to fixation;

(e) rating the fixation according to the retention of visual morphology;

(f) rating the fixation according to the preservation of cellular antigens; and (g) selecting a fixative which scores satisfactorily in terms of preservation of cellular morphology and/or preservation of cellular antigenicity, and wherein determination of the optimum hybridization conditions comprises the steps of:

(h) contacting cells from a specimen with said fixative selected in step (g);

(i) incubating said fixed specimen with said hybridization solution, said contacting being under hybridizing conditions at a temperature from 15 to 80 degrees Celsius;

(j) determining the shift of double-strandedness to single-strandedness by the cellular polynucleotides in the cells after step (i) has been performed at a desired temperature for a plurality of lengths of time by a process comprising the following four steps:

(I) staining cells with a stain able to stain polynucleotides within said cells to yield a different emission spectrum upon ultraviolet excitation of stained double-stranded and stained single-stranded polynucleotides;

(II) determining the total amount of emitted fluorescence of a cell sample not treated under hybridizing conditions;

(III) determining the total amount of emitted fluorescence of cell samples treated by various fixation and hybridization procedures and times;

(IV) assessing when the svnount of fluorescence corresponding to the amnount of double-stranded nucleic acid has decreased about 70%; and (k) Selecting the time for the incubating step (B) of the assay method as the time when about 70% of said cellular polynucleotide has shifted to single-stranded in step (j) and selecting the fixation medium of step (A) as the fixative selected in step (g) or, if about 70% of said cellular polynucleotide has not shifted to single-stranded after a desired length of time in step (j), selecting a different fixative in step (g) and performing steps (h) through (k) again.

55. The method d claim 54, wherein the fixative in step (b) is selected from the group consisting of: 95% ethanol/5% acetic acid, 75% ethanol/20% acetic acid, 50% methanol/50% acetone and 10% formaldehyde/90% methanol.

56. The method of claim 55, wherein step (i) is performed at a plurality of temperatures in the recited range, whereby the desired temperature for step (j) is determined.

57. The method of claim 56, wherein step (j) is perfomed for lengths of time from 5 to 120 minutes.

* * * * *

UNITED STATES PATENT AND TRADEMARK OFFICE
CERTIFICATE OF CORRECTION

PATENT NO. : 5,707,801
DATED : January 13, 1998
INVENTOR(S) : Joel Bresser, Mary Jean Evinger-Hodges It is certified that error appears in the above-identified patent and that said Letters Patent is hereby corrected as shown below:

Column 25,
Line 4, "polynueleotides" should read -- polynucleotides --
Line 24, "celluar" should read -- cellular --
Line 28, "spectnum" should read -- spectrum --
Line 31, "mount" should read -- amount --
Line 37, "nmount" should read -- amount --

Column 26,
Line 31, "is-carried" should read -- is carried --
Line 42, "celluar" should read -- celluar --
Line 45, "spedmna" should read -- specimen --
Line 48, "Specimen" should read -- specimen --
Line 59, "detectingduplexes" should read -- detecting duplexes --

Column 27,
Line 18, "nmottnt" should read -- amount --
Line 48, "fomation" should read -- formation --
Line 51, "chemilnminescers" should read -- chemiluminescers --
Line 53, "formarmide" should read -- formamide --

Column 28,
Line 12, "amoniuo" should read -- ammonio --
Line 33, "specirnen" should read -- specimen --
Line 39, unnder" should read -- under --
Line 43, "formnmide" should read -- formamide --
Line 56, "a at" should read -- at --
Line 61, "detecing" should read -- detecting --

Column 29,
Line 4, "straned" should read -- stranded --
Line 65-66, "maiut-nining" should read -- "maint-aining --.

Column 30,
Line 5, "polvnucleotides" should read -- polynucleotides --
Line 9, "mount" should read -- amount --
Line 10, "snmples" should read -- samples --
Line 21, "pelynucloetide" should read -- polynucleotide --
Line 36, compriagent or a cross-linking agent, said precpitaing" should read -- comprising at least one agent that is a precipitating --

UNITED STATES PATENT AND TRADEMARK OFFICE
CERTIFICATE OF CORRECTION

PATENT NO. : 5,707,801
DATED : January 13, 1998
INVENTOR(S) : Joel Bresser, Mary Jean Evinger-Hodges It is certified that error appears in the above-identified patent and that said Letters Patent is hereby corrected as shown below:

Column 30, cont'd
Line 42, "hybriclization" should read -- hybridization --
Line 49, "skift" should read -- shift --
Line 57, "fixstive" should read -- fixative --

Column 32,
Line 4, "svnount" should read -- amount --
Line 5, "amnount" should read -- amount --

Signed and Sealed this

Nineteenth Day of March, 2002

Attest:

JAMES E. ROGAN
Attesting Officer
Director of the United States Patent and Trademark Office